(12) United States Patent
Price et al.

(10) Patent No.: US 7,297,139 B2
(45) Date of Patent: Nov. 20, 2007

(54) REFASTENABLE ABSORBENT GARMENT

(75) Inventors: Cindy L. Price, Appleton, WI (US);
Suzanne M. Schmoker, Oshkosh, WI (US); Lori S. Schutkoske, Butte des Morts, WI (US); Paul T. Van Gompel, Hortonville, WI (US); Jesse Paul Sorenson, Little Chute, WI (US); Jerome S. Veith, Menasha, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 540 days.

(21) Appl. No.: 10/188,302

(22) Filed: Jul. 2, 2002

(65) Prior Publication Data
US 2003/0124303 A1 Jul. 3, 2003

Related U.S. Application Data

(60) Provisional application No. 60/303,307, filed on Jul. 5, 2001.

(51) Int. Cl.
*A61F 13/15* (2006.01)
(52) U.S. Cl. ............ 604/391; 604/385.01; 604/385.11; 604/386; 604/385.03; 604/385.23; 604/385.31; 604/387; 604/392; 604/401
(58) Field of Classification Search ........... 604/385.11, 604/391, 386, 385.01, 385.03, 385.23, 385.31, 604/387, 392, 401
See application file for complete search history.

(56) References Cited

U.S. PATENT DOCUMENTS 3,694,867 A 10/1972 Stumpf 4,340,563 A 7/1982 Appel et al.
4,590,102 A * 5/1986 Rosamilia et al. ....... 427/374.1

(Continued)

FOREIGN PATENT DOCUMENTS

EP 0 233 704 B1 7/1992

(Continued)

OTHER PUBLICATIONS

Brochure, "Choosing the Right Absorbent Product for Your Needs," *Product Selection Guide*.

(Continued)

*Primary Examiner*—Tatyana Zalukaeva
*Assistant Examiner*—Ginger Chapman
(74) *Attorney, Agent, or Firm*—Brinks Hofer Gilson & Lione

(57) ABSTRACT

A refastenable absorbent garment comprises a body panel comprising a non-woven material, and preferably a non-woven spunbond material having a pattern of discrete bonded areas. The body panel has a non-elasticized area. A hook-type fastener member comprises a high-density array of hooks with a hook density of at least about 60 hooks per square centimeter. At least a portion of the array of hooks is engaged with the non-woven material at the non-elasticized area of the body panel. In one preferred embodiment of the invention, between about 5% and 25% of the non-woven spunbond material comprises the bonded area. In another preferred embodiment, the non-woven spunbond material has a basis weight of between about 0.3 osy and about 2.0 osy. A method for making the absorbent garment, and for securing the absorbent garment to a user, also are provided.

22 Claims, 12 Drawing Sheets

U.S. PATENT DOCUMENTS

| | | | |
|---|---|---|---|
| 4,668,566 A * | 5/1987 | Braun | 442/118 |
| 4,704,114 A | 11/1987 | Wilson et al. | |
| 4,704,115 A | 11/1987 | Buell | |
| 4,743,241 A | 5/1988 | Igaue et al. | |
| 4,756,709 A | 7/1988 | Stevens | |
| 4,761,318 A | 8/1988 | Ott et al. | |
| 4,826,498 A * | 5/1989 | Koczab | 604/383 |
| 4,842,596 A | 6/1989 | Kielpikowski et al. | |
| 4,850,990 A | 7/1989 | Huntoon et al. | |
| 4,891,258 A | 1/1990 | Fahrenkrug | |
| 4,894,060 A | 1/1990 | Nestegard | |
| 4,963,140 A | 10/1990 | Robertson et al. | |
| 5,032,122 A | 7/1991 | Noel et al. | |
| 5,069,678 A | 12/1991 | Yamamoto et al. | |
| 5,087,253 A | 2/1992 | Cooper | |
| 5,242,436 A | 9/1993 | Weil et al. | |
| 5,256,231 A | 10/1993 | Gorman et al. | |
| 5,273,596 A * | 12/1993 | Newkirk | 156/73.2 |
| 5,288,546 A | 2/1994 | Roessler et al. | |
| 5,312,387 A | 5/1994 | Rossini et al. | |
| 5,326,612 A | 7/1994 | Goulait | |
| 5,330,458 A | 7/1994 | Buell et al. | |
| 5,370,634 A | 12/1994 | Ando et al. | |
| 5,380,313 A | 1/1995 | Goulait et al. | |
| 5,399,219 A | 3/1995 | Roessler et al. | |
| 5,415,649 A | 5/1995 | Watanabe et al. | |
| 5,447,508 A | 9/1995 | Numano et al. | |
| 5,449,353 A | 9/1995 | Watanabe et al. | |
| 5,516,567 A | 5/1996 | Roessler et al. | |
| 5,531,731 A | 7/1996 | Brusky | |
| 5,531,732 A * | 7/1996 | Wood | 604/391 |
| 5,540,796 A | 7/1996 | Fries | |
| 5,595,567 A | 1/1997 | King et al. | |
| 5,599,334 A | 2/1997 | Johnston et al. | |
| 5,603,708 A | 2/1997 | Seth | |
| 5,616,394 A | 4/1997 | Gorman et al. | |
| 5,624,420 A * | 4/1997 | Bridges et al. | 604/365 |
| 5,669,798 A * | 9/1997 | Koczab | 442/362 |
| 5,716,470 A | 2/1998 | Belau et al. | |
| 5,763,041 A | 6/1998 | Leak et al. | |
| 5,785,699 A | 7/1998 | Schmitz | |
| 5,795,350 A | 8/1998 | Schmitz | |
| 5,820,617 A | 10/1998 | Igaue et al. | |
| 5,830,206 A | 11/1998 | Larsson | |
| 5,836,932 A | 11/1998 | Buell et al. | |
| 5,845,375 A | 12/1998 | Miller et al. | |
| 5,858,515 A | 1/1999 | Stokes et al. | |
| 5,868,987 A | 2/1999 | Kampfer et al. | |
| 5,964,742 A * | 10/1999 | McCormack et al. | 604/380 |
| 5,997,981 A * | 12/1999 | McCormack et al. | 428/99 |
| 6,000,106 A | 12/1999 | Kampfer et al. | |
| 6,022,432 A | 2/2000 | Elsberg et al. | |
| 6,030,372 A | 2/2000 | Buell et al. | |
| 6,030,373 A | 2/2000 | Van Gompel et al. | |
| 6,036,805 A | 3/2000 | McNichols | |
| 6,045,900 A * | 4/2000 | Haffner et al. | 428/315.9 |
| D427,677 S | 7/2000 | Bruemmer-Prestley | |
| D428,143 S | 7/2000 | Schmoker et al. | |
| D428,144 S | 7/2000 | Bruemmer-Prestley et al. | |
| D428,145 S | 7/2000 | Bruemmer-Prestley et al. | |
| 6,132,410 A | 10/2000 | Van Gompel et al. | |
| 6,132,660 A | 10/2000 | Kampfer | |
| D435,103 S | 12/2000 | Schmoker et al. | |
| 6,174,303 B1 | 1/2001 | Suprise et al. | |
| 6,190,594 B1 | 2/2001 | Gorman et al. | |
| 6,217,563 B1 | 4/2001 | Van Gompel et al. | |
| 6,218,593 B1 * | 4/2001 | Torimae et al. | 604/366 |
| 6,264,641 B1 | 7/2001 | Van Gompel et al. | |
| 6,336,922 B1 | 1/2002 | Van Gompel et al. | |
| 6,361,527 B1 | 3/2002 | Van Gompel et al. | |
| 6,375,646 B1 | 4/2002 | Widlund et al. | |
| 6,508,797 B1 * | 1/2003 | Pozniak et al. | 604/385.11 |
| 2002/0115971 A1 | 8/2002 | Holmes et al. | |
| 2002/0148557 A1 | 10/2002 | Heller et al. | |

FOREIGN PATENT DOCUMENTS

| | | |
|---|---|---|
| EP | 0 570 980 | 11/1993 |
| EP | 0 570 980 A1 | 11/1993 |
| EP | 0 800 379 B1 | 10/1997 |
| EP | 0 800 808 A1 | 10/1997 |
| EP | 800808 A1 * | 10/1997 |
| EP | 0 907 510 B1 | 3/2002 |
| GB | 2 244 422 A | 12/1991 |
| GB | 2267024 A * | 11/1993 |
| GB | 2 277 866 A | 11/1994 |
| GB | 2 103 930 A | 3/1998 |
| JP | 03176053 | 7/1991 |
| JP | 3-205053 | 9/1991 |
| JP | 5-317356 | 12/1993 |
| TW | 382258 | 7/1987 |
| WO | WO 92/22274 | 12/1992 |
| WO | WO 98/35642 | 8/1998 |
| WO | WO 00/20208 | 4/2000 |
| WO | WO 00/35395 | 6/2000 |

OTHER PUBLICATIONS

Price et al., Patent Application entitled, "Absorbent Garment Having a Body Conforming Absorbent Composite," U.S. Appl. No. 09/855,200, filed May 14, 2001.

Van Gompel et al., U.S Patent Application entitled "Expandable Absorbent Garment," U.S. Appl. No. 09/855,028, filed May 14, 2001 (KC 15,960).

Van Gompel et al., U.S. Patent Application entitled "Absorbent Garment With and Extensible Backsheet," U.S. Appl. No. 09/854,904, filed May 14, 2001 (KC 15,711 and 15,756).

Fell et al., "U.S. Patent Application entitled, Absorbent Garment with Expandable Absorbent Element," U.S. Appl. No. 09/855,182, filed May 14, 2001 (KC 15,688 and 15,689).

U.S. Appl. No. 60/150,382 entitled "Pants, Refastenable Pants/Undergarments/Briefs Product Design and Process for Manufacturing on a Single Asset," filed Aug. 23, 1999 (KC 14509).

U.S. Appl. No. 60/150,327 entitled "Refastenable Pant with Perforated Front Panels," filed Aug. 23, 1999 (KC 14647).

International Search Report in PCT/US02/21037, dated May 20, 2003.

Invitation to Pay Additional Fees with Partial International Search Report for PCT Application No. US02/21036, mailed Dec. 16, 2002.

Letter dated Jan. 7, 2004 for Taiwan Patent Application No. 91115029 from Huang & Partners, Taiwan, Republic of China, 2 pages.

Written Opinion mailed May 2, 2005, PCT/US02/21036, International Filing Date Jul. 3, 2002, Kimberly-Clark Worldwide, Inc., 5 pages.

Redacted letter from Huang & Partners to Mr. Andrew D. Stover, dated May 17, 2004, pp. 1-2.

International Search Report from PCT Application No. PCT/US02/21036, dated May 9, 2003, 11 pages.

International Preliminary Examination Report for PCT/US02/21037 mailed Jul. 12, 2005, 6 pages.

European Examination Report in corresponding European Application No. 02 744 802.6, dated Nov. 9, 2005, 5 pages.

* cited by examiner

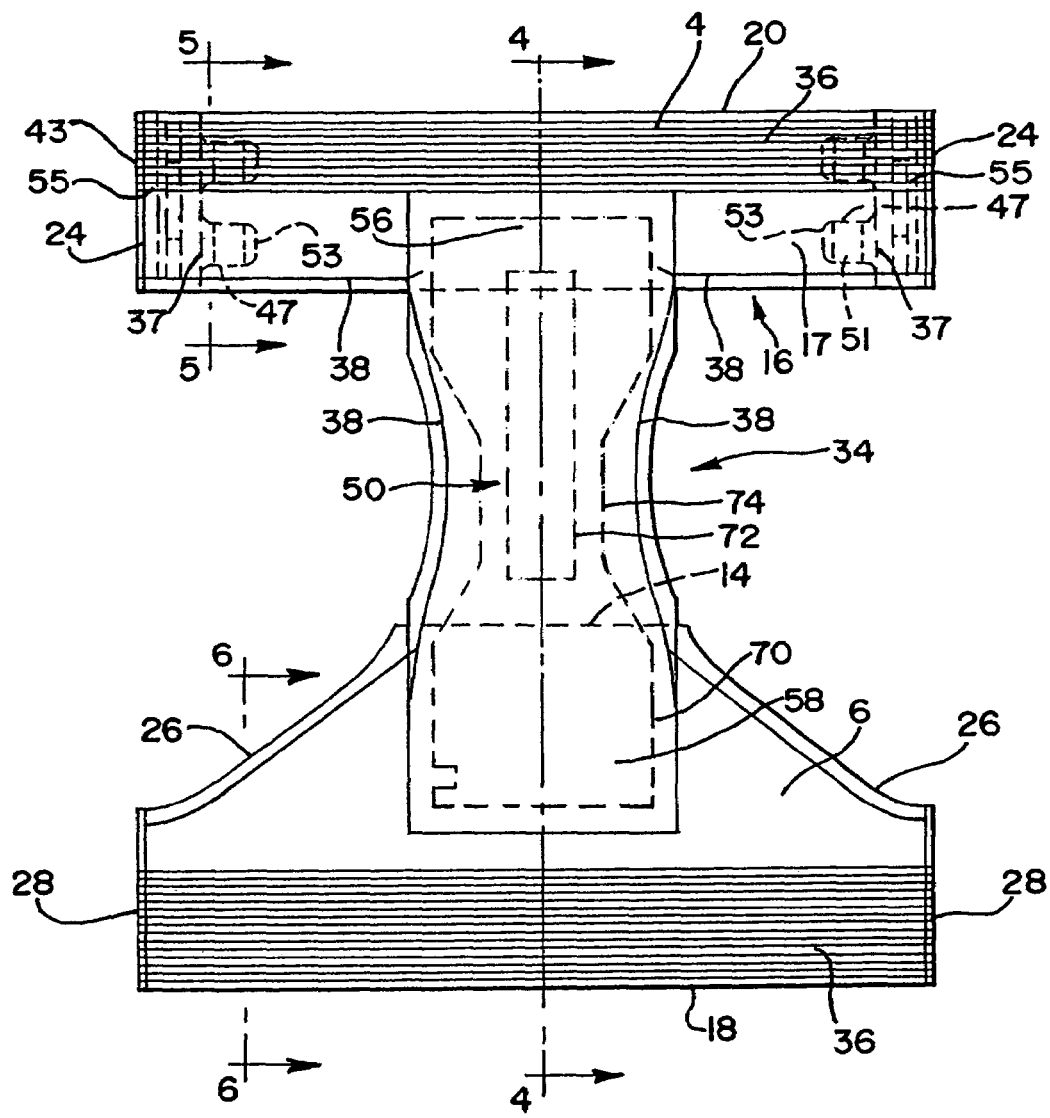

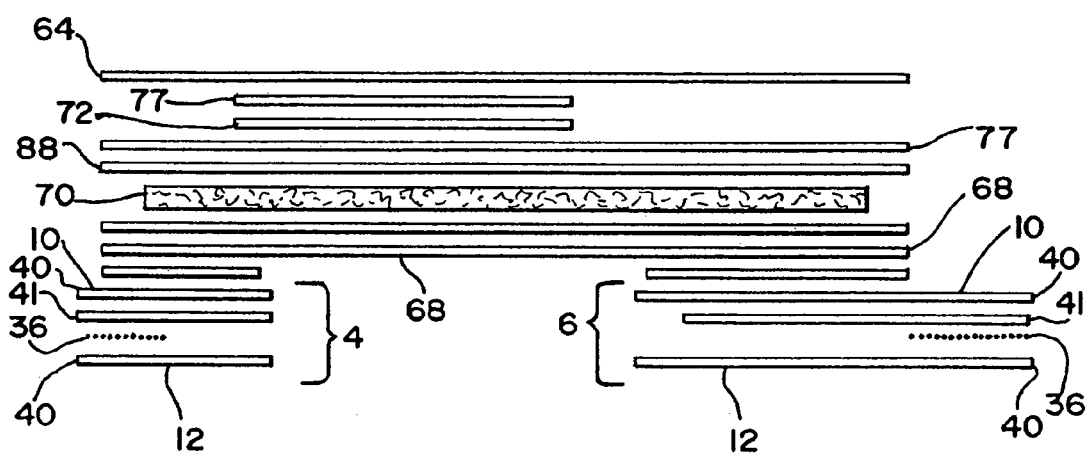
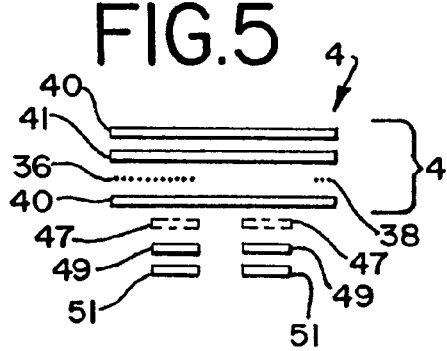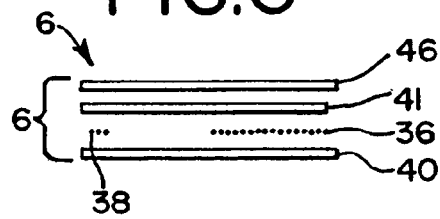

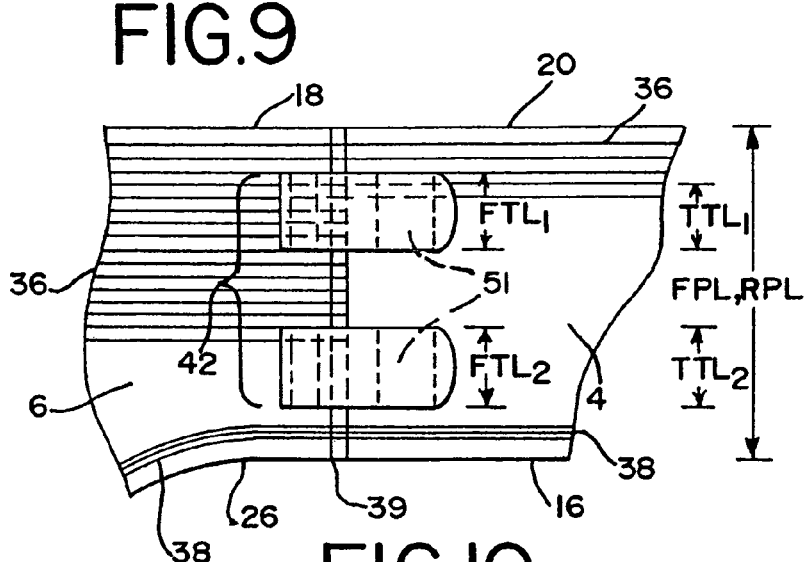
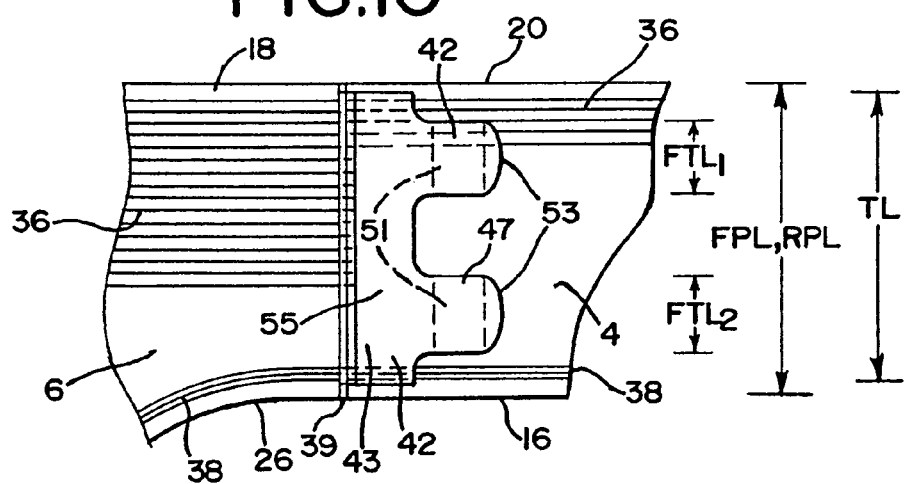
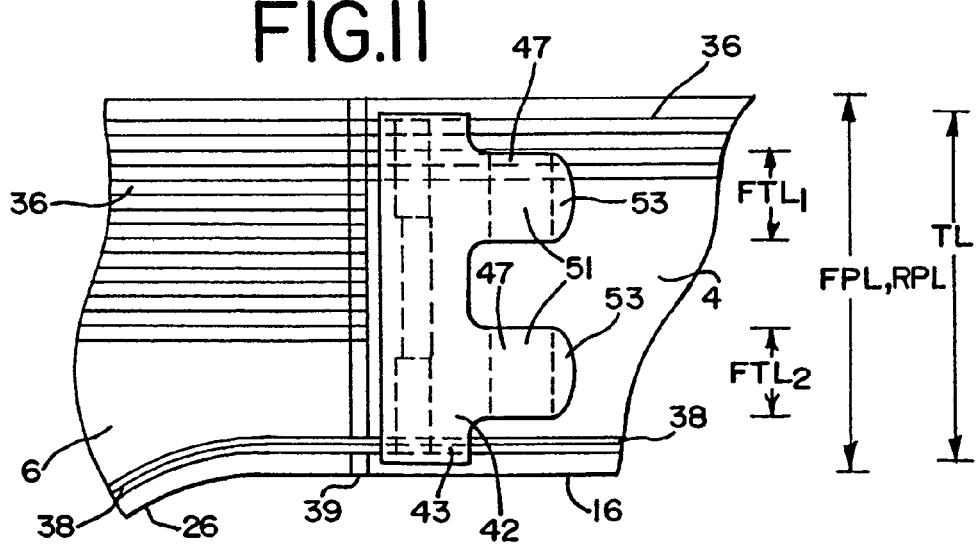

REFASTENABLE ABSORBENT GARMENT

This application claims the benefit of U.S. Provisional Application No. 60/303,307, filed Jul. 5, 2001, the entire disclosure of which is hereby incorporated herein by reference.

BACKGROUND

The present invention relates generally to a refastenable absorbent garment, and in particular, to a refastenable absorbent garment having a hook-type mechanical fastener that engages a landing member.

Absorbent garments can be configured in many different forms. For example, absorbent garments can be configured as a pant-type, pull-on garment, or as a diaper-type product that is drawn up between the legs and fastened about the waist with various fastening systems. Often, in the latter configuration, the fastening systems are configured to allow the user to detach and reattach various fasteners so as to provide a refastenable absorbent garment. For example, some fastening systems include one or more tabs that are secured to a back portion of the garment and which releasably engage a front portion of the garment.

Often, the tabs are provided with a mechanical hook system that engages a landing portion configured with loop-type material. Conventional loop-type materials can be relatively expensive to manufacture, however. In addition, the loop-type material is typically formed as a separate patch of material, which is attached to an underlying backsheet or body panel. The additional material, and the step of incorporating the patch into the garment, can add to the overall cost of the product.

In other garments, the landing portion may include an elastic member or elastomeric material, which can shirr portions of the landing portion material and thereby make it more susceptible to entanglement with the hook-type fasteners. Such aspects can increase the bulk of the garment beneath the clothes of the user, and can incur further expense in the manufacture thereof by virtue of the requirement for the additional elastic material.

SUMMARY

Briefly stated, in one aspect, the invention is directed to an absorbent garment comprising a body panel comprising a non-woven material. In one embodiment, the non-woven material is a spunbond material having a pattern of discrete bonded areas. The body panel has a non-elasticized area. A hook-type fastener member comprises a high-density array of hooks with a hook density of at least 60 hooks per square centimeter. At least a portion of the array of hooks is engaged with the non-woven material at the non-elasticized area of the body panel.

In one preferred embodiment of the invention, between about 5% and 25% of the non-woven material comprises the bonded area. In another preferred embodiment, the non-woven material has a basis weight of between about 0.3 osy and about 2.0 osy.

In another aspect of the invention, an absorbent garment comprises a front body panel comprising opposite side edges and a rear body panel comprising opposite side edges, wherein the opposite side edges of the front and rear body panels are joined to form a side seam. A hook-type fastener member comprises a carrier member secured to the front body panel in front of the side seam and a plurality of hooks, wherein at least a portion of the plurality of the hooks are engaged with the front body panel.

In one preferred embodiment, the front body panel comprises a pair of side portions defining the opposite side edges which are mounted to the opposite side edges of the rear body panel. A landing member extends between the side portions, wherein the hooks are engaged with the landing member. In a preferred embodiment, the side portions are initially breakably attached to opposite sides of the landing member along respective lines of weaknesses.

In one preferred embodiment, the entire thickness of one or more of the body panels is a non-woven material. In another preferred embodiment, the entire outer, garment side surface of the body panel is made of the same non-woven material. In one embodiment, the one or more body panels are made of two or more substrates or layers or of a non-woven material that are bonded one to the other. In one preferred embodiment, elastic members are disposed between the bonded substrates or layers. In alternative embodiments, the elastic members can be secured on top or below the material, along one or more surfaces.

In yet another aspect of the invention, an absorbent garment comprises a body panel having a length and a fastening member comprising at least two engagement portions releasably engaging the body panel. Each of the engagement portions having an engagement length, wherein the sum of the engagement lengths is at least about 20% of the body panel length.

In another aspect, the body panel comprises a front body panel. A rear body panel, having a length, is secured to the front body panel along a seam, which has a length. The fastening member comprises a carrier member having a length. In one preferred embodiment, the length of the carrier member is at least about 50% of the length of the seam. In another preferred embodiment, the length of the carrier member is at least about 50% of the length of the rear body panel.

In another aspect of the invention, a method of securing an absorbent garment to a user is provided. In yet another aspect, a method of manufacturing an absorbent garment is provided.

The present invention provides significant advantages over other absorbent garments and methods for the use and manufacture thereof. For example, the body panel can be made out of a relatively low basis weight non-woven material, which provides a landing area for the hook-type fasteners without the need for an additional loop-type material. In this way, the absorbent garment can be made with less expense. For example, in one embodiment, the body panel is made of one or more substrates of non-woven material, which is relatively inexpensive to manufacture yet provides a soft and flexible surface that contacts the user's body. In addition, portions of the body panel can be made without elastic members so as to provide a better fit for the user that has a less bulky appearance, and which reduces the overall expense of the garment. In addition, by making the absorbent garment refastenable, it can be applied without needing to pull it on or off like a pant-like garment. In addition, the garment can be made bigger or smaller simply by adjusting the positioning of the fasteners.

Moreover, in one particular application, wherein the garment is used by adults, for example with occasional incontinence problems, the fastening system may be disengaged and engaged repeatedly by the user while the garment remains unsoiled over an extended period of time. At the same time, the garment can initially be pulled on like a pant-like garment before the lines of weaknesses are broken. The non-woven materials disclosed and described herein do not tend to become stringy and the fibers do not tend to pull away from the garment, as is experienced with some loop materials. As such, the material provides a landing area that is particularly suited for repeated engagements with the hook-type fastening members, and in particular, high-density hook-type fasteners.

In addition, the fastener member, with its at least two engagement portions releasably engaging the body panel, allows the user to independently control both the waist region and the leg region of the front body panel, while also providing the user with a pant-like fit. At the same time, the user can adjust one or the other of the engagement portions without the garment coming undone. The total length of the engagement portions controls a larger area of the body panel. At the same time the length of the carrier member provides the user with control of the body panel.

The present invention, together with further objects and advantages, will be best understood by reference to the following detailed description taken in conjunction with the accompanying drawings.

BRIEF DESCRIPTION OF THE DRAWINGS

Many of the features and dimensions portrayed in the drawings, and in particular the presentation of layer thicknesses and the like, have been somewhat exaggerated for the sake of illustration and clarity.

FIG. 3 is a bodyside plan view of another embodiment of an absorbent garment in an unfastened flat configuration.

FIG. 4 is an exploded cross-sectional view of the absorbent garment taken along line 4-4 in FIG. 3.

FIG. 5 is an exploded cross-sectional view of the absorbent garment taken along line 5-5 in FIG. 3.

FIG. 6 is an exploded cross-sectional view of the absorbent garment taken along line 6-6 in FIG. 3.

FIG. 9 is partial side view of one preferred embodiment of an absorbent garment fastening system.

FIG. 10 is partial side view of an alternative preferred embodiment of an absorbent garment fastening system.

FIG. 11 is partial side view of an alternative preferred embodiment of an absorbent garment fastening system.

DETAILED DESCRIPTION OF THE PRESENTLY PREFERRED EMBODIMENTS

It should be understood that the term "longitudinal," as used herein, means of or relating to length or the lengthwise direction, and in particular, the direction running between the front and back of the user. The term "laterally," as used herein means situated on, directed toward or running from side to side, and in particular, a direction running from the left to the right of a user, and vice versa. The terms "upper," "lower," "inner," and "outer" as used herein are intended to indicate the direction relative to the user wearing an absorbent garment over the crotch region, while the terms "inboard" and "outboard" refer to the directions relative to a centerline 8 of the garment. For example, the terms "inner" and "upper" refer to a "bodyside," which means the side closest to the body of the user, while the terms "outer" and "lower" refer to a "garment side."

The term "bodyside" should not be interpreted to mean in contact with the body of the user, but rather simply means the side that would face toward the body of the user, regardless of whether the absorbent garment is actually being worn by the user and regardless of whether there are or may be intervening layers between the component and the body of the user. Likewise, the term "garment side" should not be interpreted to mean in contact with the garments of the user, but rather simply means the side that faces away from the body of the user, and therefore toward any outer garments that may be worn by the user, regardless of whether the absorbent garment is actually being worn by a user, regardless of whether any such outer garments are actually worn and regardless of whether there may be intervening layers between the component and any outer garment.

Figure 1:
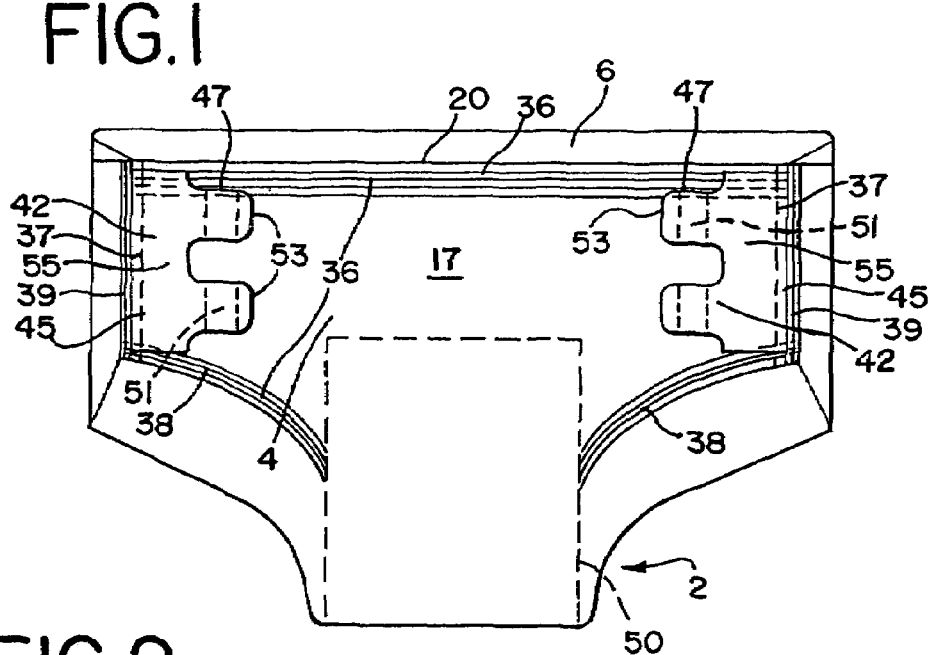
FIG. 1 is a front view of one embodiment of an absorbent garment in a fastened configuration.
Figure 2:
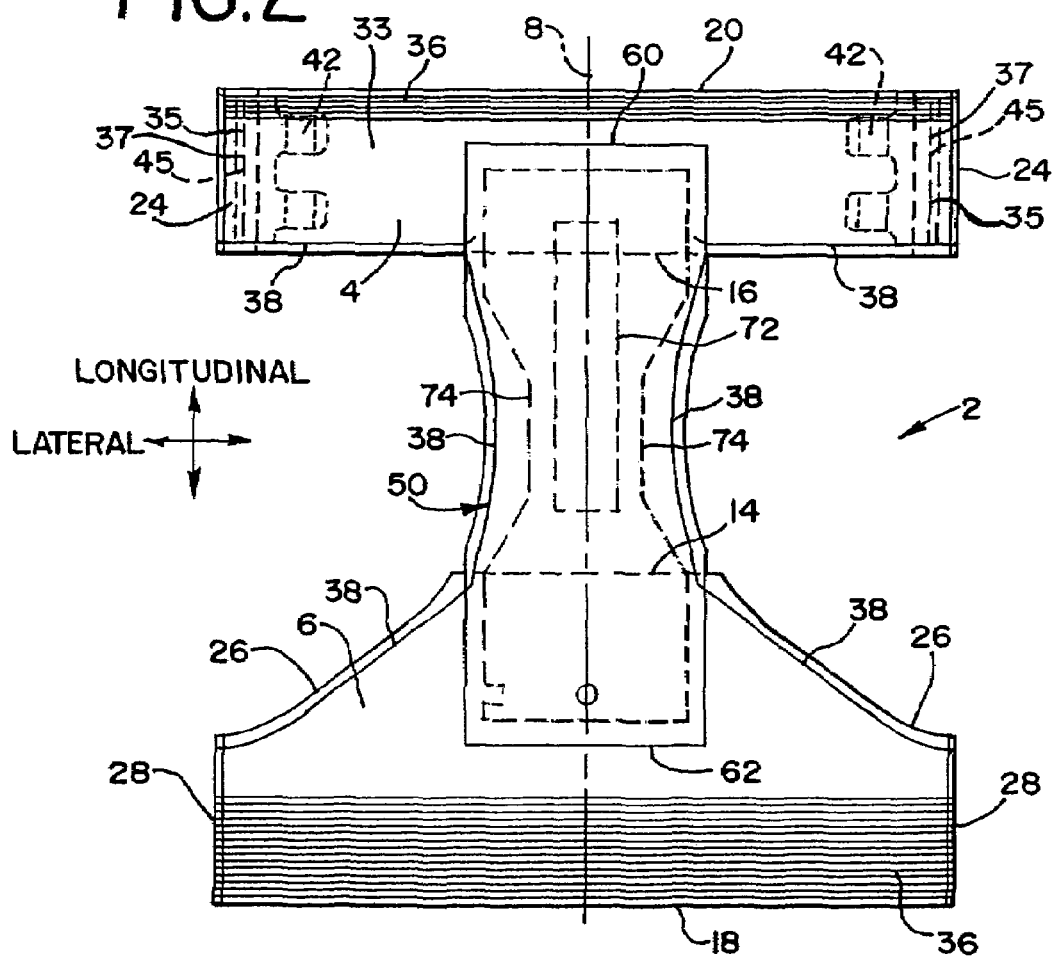
FIG. 2 is a bodyside plan view of one embodiment of an absorbent garment in an unfastened flat configuration.

Referring to FIGS. 1-6, an absorbent garment 2 includes a first, front body panel 4 and a second, rear body panel 6. The first and second body panels each have an inner, bodyside surface 10 and an outer, garment side surface. The first, front body panel 4 has a length (FPL), which is measured between opposed first and second terminal edges 16 and 20, as shown in FIGS. 9-11, and which is less than the overall length of the absorbent garment. Likewise, the second, rear body panel 6 has an overall length (RPOL), which is measured between opposed first and second terminal edges 14 and 18, as shown in FIGS. 2 and 3, and which is also less than the overall length of the absorbent garment. Each of the first and second body panels has an outboard edge 24, 28 formed along the outer periphery of laterally opposed side portions of the first and second body panel. The outboard edge of the second body panel 6 has a length (RPL), which is preferably the same length (FPL) of the front body panel. It should be understood that the outboard edges of the front and rear body panels can be different lengths.

As shown in FIGS. 2 and 3, the second body panel also includes opposite tapered edges 26. The first terminal edges 14, 16 of the first and second body panels are longitudinally spaced to form an opening 34 therebetween in the crotch region of the garment, while the second terminal edges 20, 18 of the first and second body panels form front and back waist edges respectively.

Referring to FIGS. 1-6, one or more, and preferably a plurality, meaning two or more, laterally extending elastic elements 36 are secured to each of the first and second body panels along the terminal edges 20, 18. Preferably, a plurality of laterally extending elastic elements are longitudinally spaced across substantially the entire length of the waist portion of the rear body panel 6, although they may be spaced across a lesser length. In various preferred embodiments, at least one, and preferably between about 16 and 21 laterally extending elastic elements are longitudinally spaced along the length of the body panel. For example, in one embodiment, the elastic elements are spaced about 0.25 inches from each other. It should be understood, that in an alternative embodiment, one or more separate waist bands, with or without elastic elements, can be secured to one or both of the rear and front body panels, preferably along the upper terminal edges thereof.

The front body panel preferably has a "non-elasticized" area 17 wherein there are no laterally extending elastic elements, or other elastic or elastomeric backing members, incorporated therein or making up any portion of the thickness or cross-section of the body panel at that area, such that the material can be gathered. Preferably, one or more elastic elements 36 extend laterally along the outer terminal edge 20 and are longitudinally spaced along about a one-inch wide portion of the front body panel. In this embodiment, the non-elasticized area 17 is formed between the elastic elements 36 extending along the upper waist portion and elastic elements 38 extending along the lower terminal edge defining the leg opening. In various embodiments, at least one, and preferably from about 4 to about 11 elastic elements are spaced along the upper waist portion of the front body panel. One or more leg elastic elements 38 can be secured along the inner terminal edges of the body panels 4, 6 and an absorbent composite 50 to form a gasket with the leg of the user.

In addition, the term "non-elasticized" should further be understood as also meaning non-gathered, wherein the material does not have any pillows, ripples or other substantially three-dimensional undulations or aspects associated therewith, regardless of whether such gathered material is formed by incorporating various elastic elements, or by bonding various non-elastic layers, one or more of which may be stretched, to other layers having a different surface area, as disclosed for example in U.S. Pat. No. 5,763,041, which is hereby incorporated herein by reference. Rather, the material lies substantially flat in the non-elasticized area.

The various waist and leg elastic elements can be formed from rubber or other elastomeric materials. One suitable material is a LYCRA® elastic material. For example, the various elastic elements can be formed of LYCRA® XA Spandex 540, 740 or 940 detex T-127 or T-128 elastics available from E.I. duPont De Nemours and Company, having an office in Wilmington, Del.

As shown in FIGS. 4-6, each body panel is preferably formed as a composite, or laminate material comprising two non-woven layers 40, otherwise referred to as substrates or laminates, with the plurality of elastic strands 38, 36 sandwiched therebetween. The elastic strands 36, 38 are positioned in the waist regions and along the leg perimeters as explained above. The two layers 40 are then bonded with various adhesives 41, such as hot melt, or by other techniques, including for example and without limitation ultrasonic bonding and heat pressure sealing. In this way, the body panels are preferably made of a relatively homogenous non-woven material, whether made of one or more layers or substrates, and preferably without any additional film materials or other types of materials being laminated thereto. As such, the body panels can be made with a relatively low basis weight, yet still exhibit requisite strength properties while remaining relatively soft to the touch. It should be understood that the body panels can be made of a single layer or substrate of non-woven material, or can be comprised of more than two layers or substrates.

At the same time, it should be understood that at least the outermost substrate, layer or web of the body panel is preferably constructed of the non-woven materials described herein. The non-woven material preferably makes up and defines the entire outer, garment-side surface of the body panel, and is preferably a relatively homogenous material over the entire extent of the body-panel, without the addition of any additional landing materials secured thereto. Of course, it should be understood that other knitted or woven fabrics, non-woven fabrics, polymer films, laminates and the like can be secured, by bonding or other lamination techniques, to the bodyside surface of the outermost non-woven material substrate. The term "non-woven" web or material, as used herein, means a web having a structure of individual fibers or filaments that are interlaid, but not in an identifiable manner and without the aid of textile weaving or knitting, as in a knitted or woven fabric.

Figure 7:
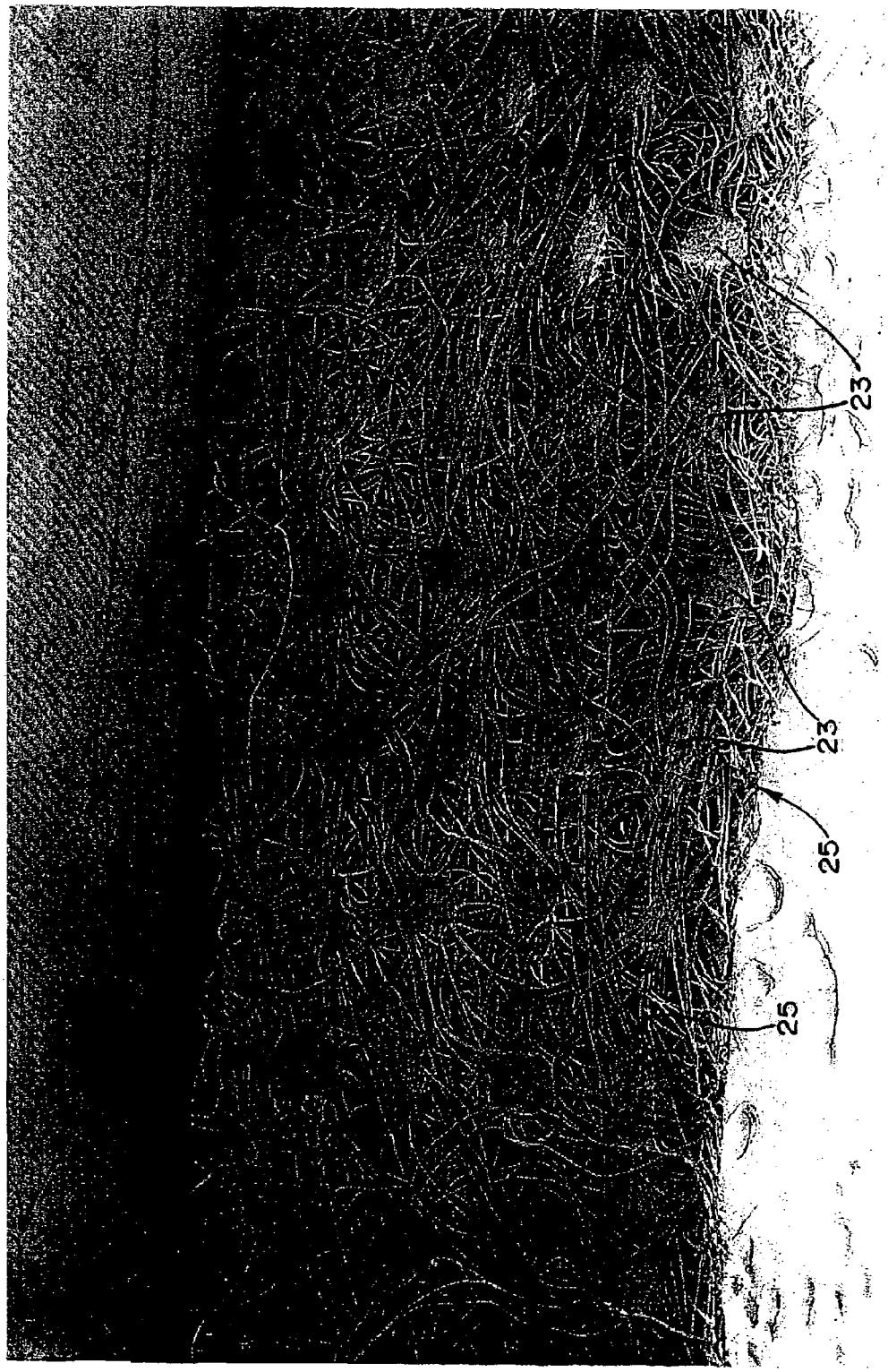
FIG. 7 is an enlarged plan view of the front body panel material.

The non-woven layers or substrates 40 are preferably made by spunbonding. Spunbond nonwoven webs or materials are made from melt-spun filaments or spunbonded fibers 25, shown in FIGS. 7 and 8, which refers to small diameter fibers that are formed by extruding molten thermoplastic material as filaments from a plurality of fine, usually circular capillaries of a spinneret with the diameter of the extruded filaments then being rapidly reduced, for example, by non-eductive or eductive fluid-drawing or other well known spunbonding mechanisms. The production of spunbound nonwoven webs is described in U.S. Pat. No. 4,340,563 to Appel et al., U.S. Pat. No. 3,692,618 to Dorschner et al., U.S. Pat. No. 3,802,817 to Matsuki et al, U.S. Pat. No. 3,502,763 to Hartmann, U.S. Pat. No. 3,276,944 to Levy, U.S. Pat. No. 3,502,538 to Peterson, and U.S. Pat. No. 3,542,615 to Dodo et al, all of which are incorporated herein by reference. The melt-spun filaments formed by the sponbond process are generally continuous and have diameters larger than 7 microns, more particularly, between about 10 and 30 microns. Another frequently used expression of fiber or filament diameter is denier, which is defined as grams per 9000 meters of a fiber or filament. The fibers may also have shapes such as those described in U.S. Pat. No. 5,277,976 to Hogle, et al, U.S. Pat. No. 5,466,410 to Hills and U.S. Pat. Nos. 5,069,970 and 5,057,368 to Largman et al., all of which are incorporated herein by reference. The spunbond filaments usually are deposited, by one or more banks, onto a moving foraminous belt or forming wire where they form a web. Spunbonded filaments generally are not tacky when they are deposited onto the collecting surface.

Spunbond fabrics typically are stabilized or consolidated (pre-bonded) in some manner immediately as they are produced in order to give the web sufficient integrity to withstand the rigors of further processing into a finished product. This stabilization (prebonding) step may be accomplished through the use of an adhesive applied to the filaments as a liquid or powder which may be heat activated, or more commonly, by compaction rolls. As used herein, the term "compaction rolls" means a set of rollers above and below the web used to compact the web as a way of treating a just produced, melt-spun filament, particularly spunbond, web, in order to give the web sufficient integrity for further processing, but not the relatively strong bonding of secondary bonding processes, such as through-air bonding, thermal bonding, ultrasonic bonding and the like. Compaction rolls slightly squeeze the web in order to increase its self-adherence and thereby its integrity.

An alternative means for performing the pre-bonding step employs a hot air knife, as described in U.S. patent application Ser. No. 362,328, filed Dec. 22, 1994, which is incorporated herein by reference. Briefly, the term "hot air knife" means a process of pre-bonding a just produced melt-spun filament, particularly spunbond, web, in order to impart the web with sufficient integrity, i.e., increase the stiffness of the web, for further processing. A hot air knife is a device that focuses a stream of heated air at a very high flow rate, generally from about 300 to about 3000 meters per minute (mi/min.), or more particularly from about 900 to about 1500 m/min., directed at the nonwoven web immediately after its formation. The air temperature usually is in the range of the melting point of at least one of the polymers used in the web, generally between about 90° C. and about 290° C. for the thermoplastic polymers commonly used in spunbonding. The control of air temperature, velocity, pressure, volume and other factors helps avoid damage to the web while increasing its integrity.

The hot air knife's focused stream of air is arranged and directed by at least one slot of about 3 to about 25 millimeters (mm) in width, particularly about 9.4 mm, serving as the exit for the heated air towards the web, with the slot running in a substantially cross-machine direction over substantially the entire width of the web. In other embodiments, there may be a plurality of slots arranged next to each other or separated by a slight gap. The at least one slot usually, but not necessarily, is continuous, and may be comprised of, for example, closely spaced holes. The hot air knife has a plenum to distribute and contain the heated air prior to its exiting the slot. The plenum pressure of the hot air knife usually is between about 2 to about 22 mmHg, and the hot air knife is positioned between about 6.35 mm and about 254 mm, and more particularly from about 19.05 to about 76.20 mm above the forming surface. In a particular embodiment, the hot air knife plenum's cross-sectional area for cross-directional flow (i.e., the plenum cross-sectional area in the machine direction) is at least twice the total slot exit area. Since the foraminous wire onto which spunbond polymer is formed generally moves at a high rate of speed, the time of exposure of any particular part of the web to the air discharge from the hot air knife typically is less than a tenth of a second and generally about one hundredth of a second, in contrast with the through-air bonding process, which has a much longer dwell time. The hot air knife process has a great range of variability and control over many factors, including air temperature, velocity, pressure, and volume, slot or hole arrangement, density and size, and the distance separating the hot air knife plenum and the web.

The spunbond process also can be used to form bicomponent spunbond nonwoven webs as, for example, from side-by-side (or sheath/core) linear low density polyethylene/polypropylene spunbond bicomponent filaments. A suitable process for forming such bicomponent spunbond nonwoven webs is described in U.S. Pat. No. 5,418,045 to Pike et al., which is incorporated herein by reference in its entirety.

Commercially available thermoplastic polymeric materials can be advantageously employed in making the fibers or filaments from which pattern-unbonded nonwoven material 4 is formed. As used herein, the term "polymer" shall include, but is not limited to, homopolymers, copolymers, such as, for example, block, graft, random and alternating copolymers, terpolymers, etc., and blends and modifications thereof. Moreover, unless otherwise specially limited, the term "polymer" shall include all possible geometrical configurations of the material, including, without limitation, isotactic, syndiotactic and random symmetries. As used herein, the terms "thermoplastic polymer" or "thermoplastic polymeric material" refer to a long-chain polymer that softens when exposed to heat and returns to its original state when cooled to ambient temperature. Preferably, the spunbond fibers are made of a polypropylene. Other alternative thermoplastic materials include, without limitation, poly (vinyl chloride)s, polyesters, polyamides, polyfluorocarbons, polyolefins, polyurethanes, polystyrenes, polyethylenes, poly(vinyl alcohol)s, caprolactams, and copolymers of the foregoing. The fibers or filaments used in making the nonwoven material may have any suitable morphology and may include hollow or solid, straight or crimped, single component, bicomponent or multicomponent, biconstituent or multiconstituent fibers or filaments, and blends or mixes of such fibers and/or filaments, as are well known in the art.

After the nonwoven web is formed, the pre-bonded or unbonded web is passed through a suitable process or apparatus, including for example a calendar roll, to form a pattern of discrete bonded areas. The term "discrete" as used herein means individual or disconnected, and is contrasted with the term "continuous" as used in U.S. Pat. No. 5,858,515 to Stokes et al, which describes pattern-unbonded, or point un-bonded (PUB), nonwoven fabrics having continuous bonded areas defining a plurality of discrete unbonded areas. In one embodiment, the calendar stack (not shown) includes an anvil roll and a pattern roll, which is heated and includes various raised landing portions. The raised portions of the pattern roll thermally bond the fibers to form the bonded areas 23, as shown for example in FIG. 7. The bonds can made of any shape and size. Preferably, the percent bonded area of the web is between about 5% and 25% of the area of the web, and is more preferably between about 10% and 15%. Thereafter, the bonded substrate can be bonded to another substrate with the elastic members disposed therebetween.

In the various configurations of the invention, the basis weight of each of the body panel non-woven spunbond material substrates is preferably about 0.6 osy. In other preferred embodiments, the basis weight of each substrate can be between at least about 0.3 and about 2.0 osy, and preferably between about 0.5 osy and about 1.5 osy, and more preferably between about 0.5 osy and about 1.0 osy. Even with a relatively low percent area bonding, the relatively low basis weight non-woven spunbond material exhibits strength and tear characteristics allowing it to be used as a body panel. Other materials that may be used as the non-woven material include various meltblown materials, and also bonded-carded materials.

The body panels 4, 6 non-woven material is preferably substantially hydrophobic, which may optionally be treated with a surfactant or otherwise process to impart a desired level of wettability and hydrophilicity. In one particular embodiment of the invention, the body panel is a nonwoven, wire-weave spunbond polypropylene fabric composed of about 1.6 denier fibers formed into a web having a basis weight of about 0.6 osy. One suitable non-woven material is the Corinth 0.60 osy, 1.6 dpf wireweave, nonwettable Metallocene (EXXON ACHIEVE 2854 PP) Spunbond material manufactured by Kimberly-Clark Corporation, the assignee of the present application.

The preferred non-woven materials, which are relatively smooth can be distinguished from other non-woven materials that have been used as loop materials by a comparison of various properties. For example, and referring to FIGS.

12-15, Scanning White-Light Interference Microscopy (SWLIM) tests were performed on two materials, a 0.60 osy wire-weave spunbond laminate material and a 2.0 osy point-unbonded (PUB) material to determine various roughness parameters. The 2D and 3D representations of FIGS. 12-15 are each a 3×3 field montage, having a size of about 6.7 mm×5.1 mm. The results of the SWLIM tests are referenced in Table 1.

TABLE 1

SWLIM Tests

|  | Ra | Rku* | RP | RPm | Rq | Rsk* | Rt | Rv | Rvm | Rz |
|---|---|---|---|---|---|---|---|---|---|---|
| 2.0 osy PUB | 232388.8 | 2.03 | 920876.1 | 880239.5 | 261447.7 | 0.61 | 1399770 | −478894.1 | −478459.2 | 1358699 |
| 0.6 osy spunbond | 59685.93 | 5.15 | 301757.1 | 280871.7 | 81723.13 | −0.73 | 725239.3 | −423482.3 | −413034.9 | 693906.6 |

*Rku, Rsk - no units
All other measurements are in nanometers

As used in Table 1, Ra is the "roughness average," which is defined as the mean height of the surface calculated over the entire array. Effects of single spurious peaks are averaged out. Ra may average out detail needed to quantify a complex surface. Rq is the "root mean square roughness" (rms), which is defined as the rms average of the measured height deviations taken within the evaluation area and measured from the mean linear surface. Rq is used to calculated skewness and kurtosis. If a surface has a profile that contains no large deviations from the mean surface level, the values of Ra and Rq will be similar. If there are appreciable numbers of large bumps or holes, the largest values of the profile height function will dominate the surface statistics and Rq will be larger than Ra. Rt is the "maximum height of the profile," which is defined as the vertical distance between the highest and the lowest points on the evaluation area. Rz is the "average maximum height of the profile," which is defined as the average of the greatest peak-to-valley separations. Rpm is the "average maximum profile peak height," which is defined as the mean peak height of the entire dataset. Rpm characterizes surface based on peaks in the surface profile. Rvm is the "average maximum profile valley depth," which is defined as the mean peak valley for the entire data set. Rsk is the "skewness," which is defined as a measure of the asymmetry of the profile. The sign of the skewness will tell whether the farther points are proportionately above (positive skewness) or below (negative skewness) the mean surface level. Rku is the "kurtosis," which is defined as the measure of the peakedness of the profile. A random surface will have a kurtosis value close to 3. The farther the kurtosis value is from 3, the less random (the more repetitive) the surface is. A smooth surface with few high and low extreme points will have a value less than 3. Rv is the "maximum profile valley depth," which is defined as the maximum depth of the profile below the mean line for the entire data set. Rp is the "maximum profile peak height," which is the maximum height of the profile above the mean line for the entire data set.

Figure 12:
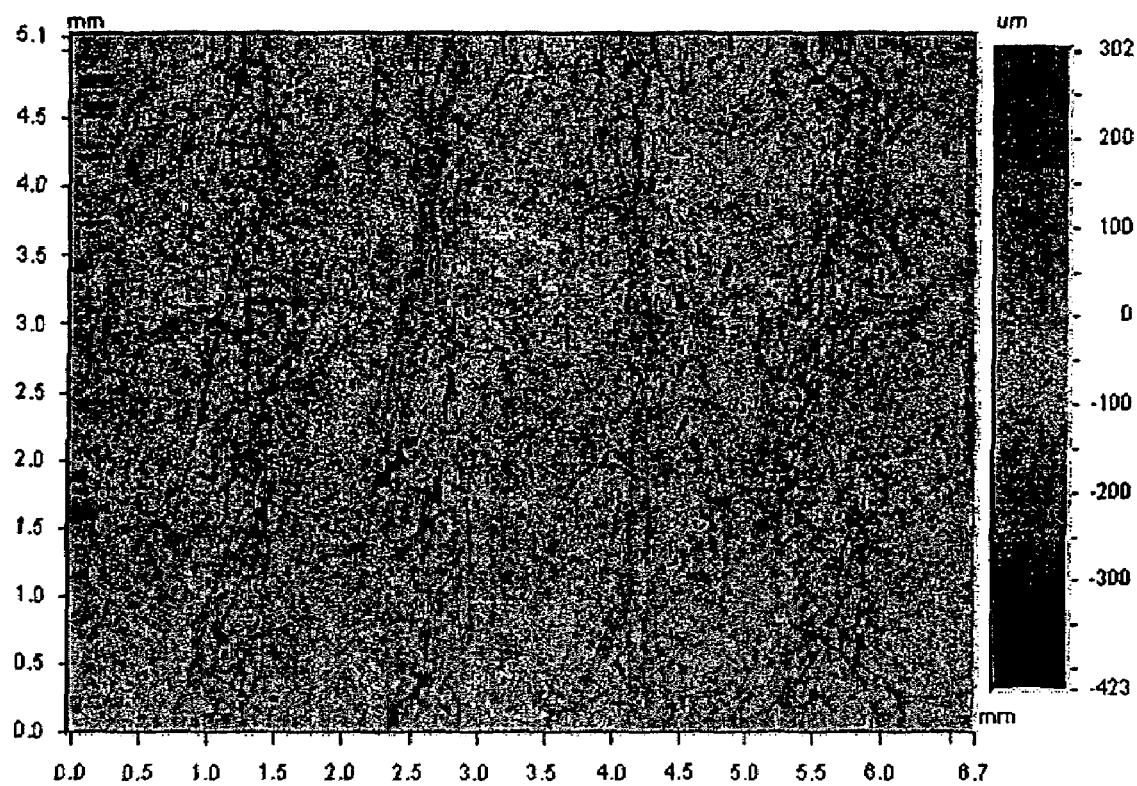
FIG. 12 is a two-dimensional rendition of a surface of a non-woven spunbond material.
Figure 13:
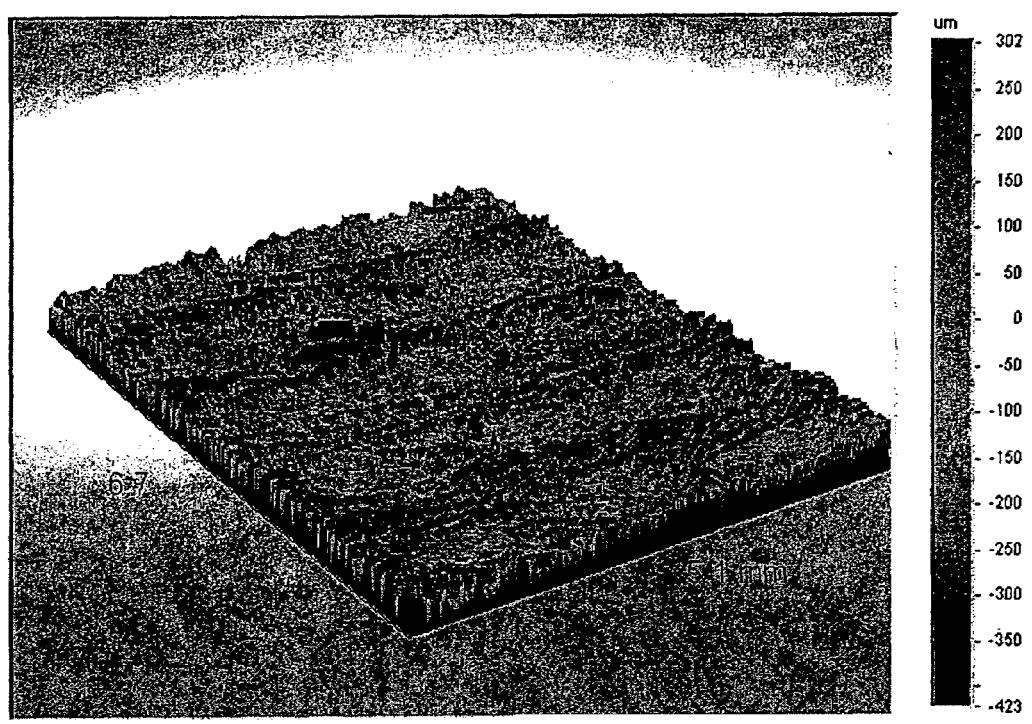
FIG. 13 is a three-dimensional rendition of the surface of the non-woven spunbond material shown in FIG. 12.
Figure 14:
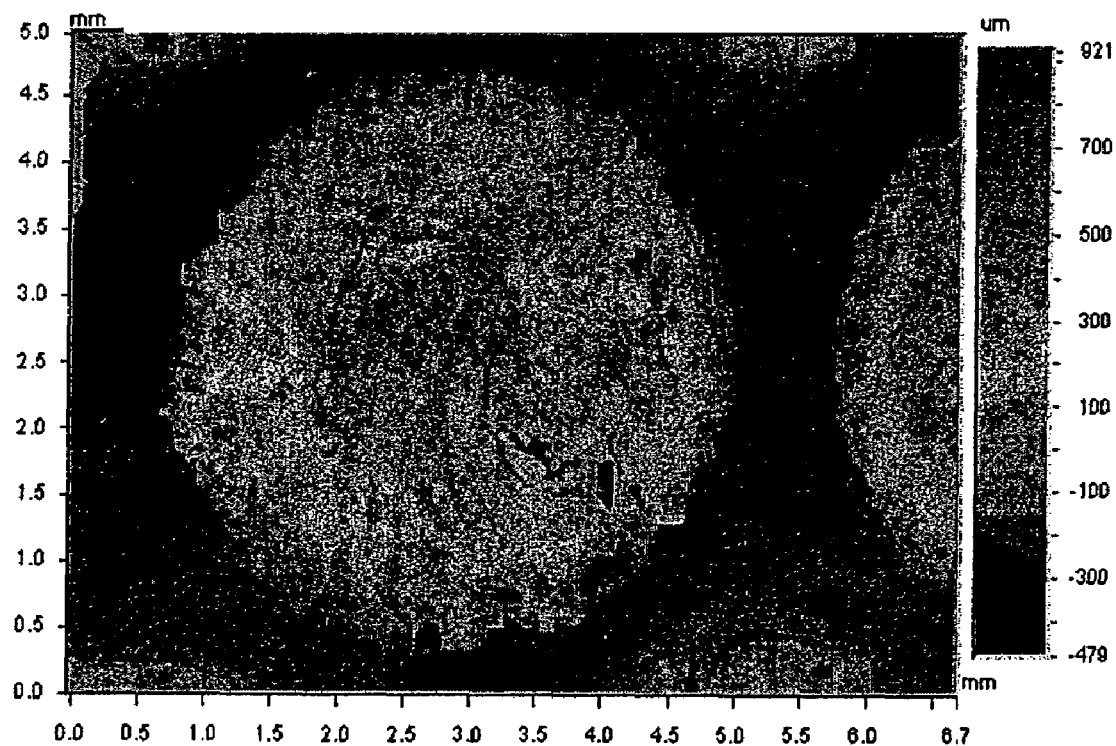
FIG. 14 is a two-dimensional rendition of a surface of a non-woven point unbonded material.
Figure 15:
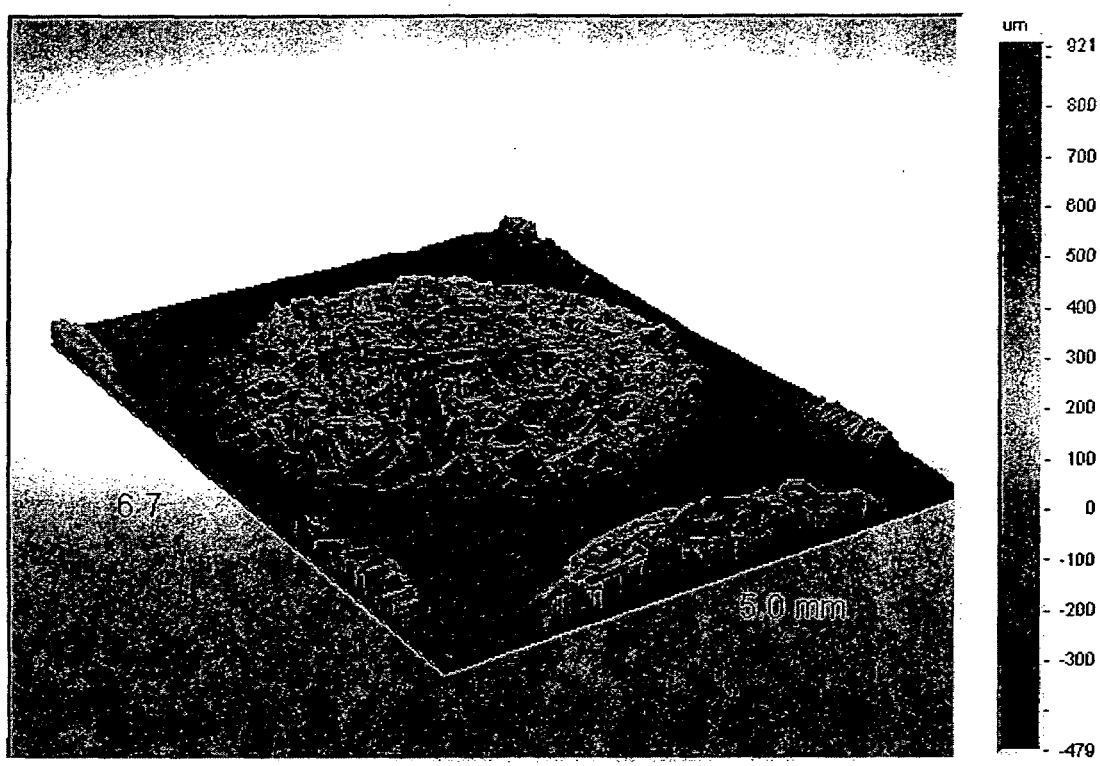
FIG. 15 is a three-dimensional rendition of the surface of the non-woven point unbonded material shown in FIG. 14.

As can be seen from Table 1, and FIGS. 12 and 13, the preferred non-woven spunbond material has a considerably lower roughness average (Ra) and root mean square roughness (Rq) than the PUB material. At the same time, the non-woven spunbond material can be engaged by high-density hook materials, described herein below, to provide adequate shear and peel strength, so as to maintain the garments on the user during normal wearing conditions. In various preferred embodiments, Ra is less than about 200 um, preferably less than about 150 um, and more preferably less than about 100 um, and even more preferably less than about 70 um. Also in various preferred embodiments, Rq is less than about 250 um, preferably less than about 200 um, and more preferably less than about 150 um, and even more preferably less than about 100 um.

Figure 16:
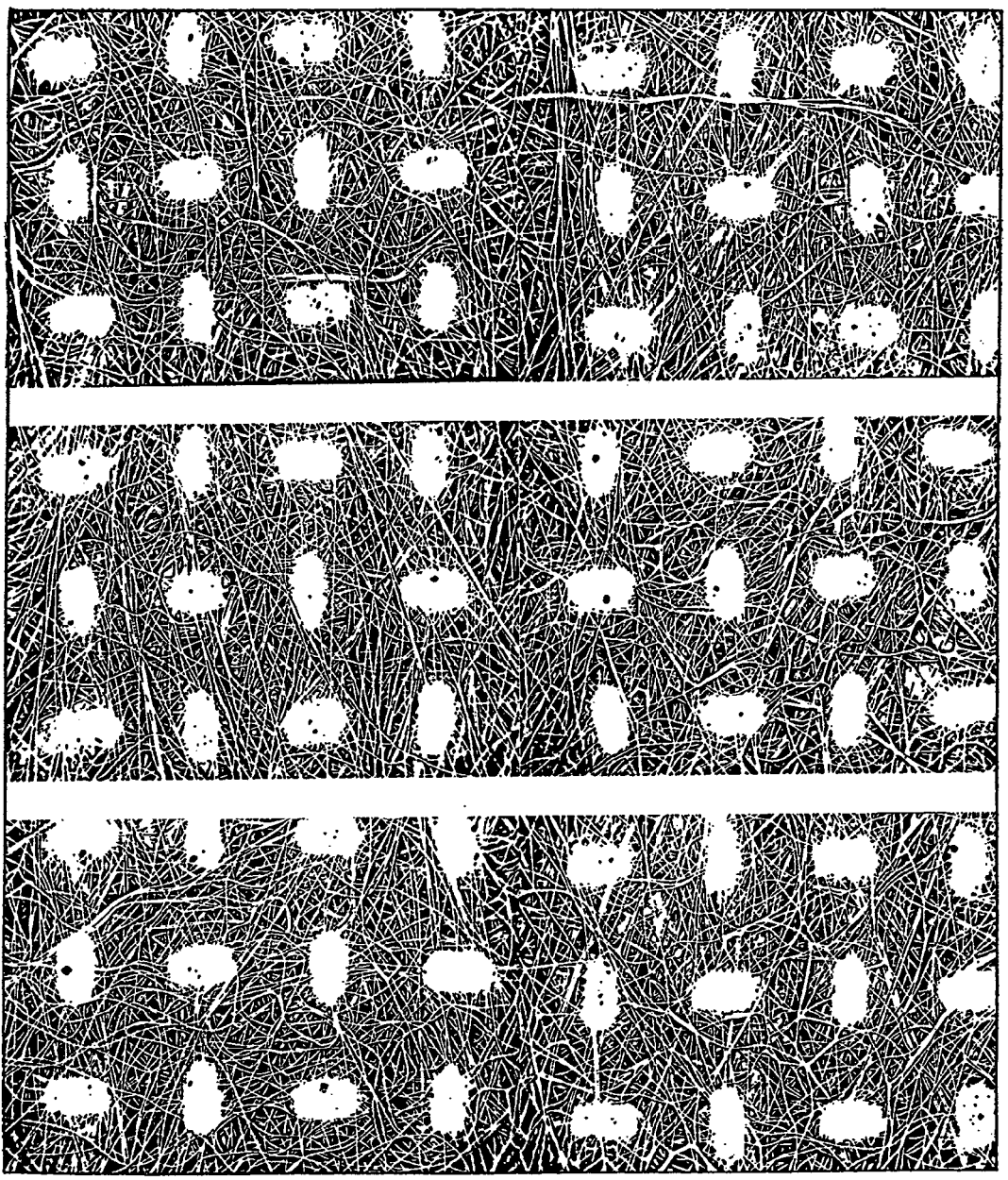
FIG. 16 is a BSE/HICON photomontage of a non-woven spunbond material at 20× magnification.
Figure 17:
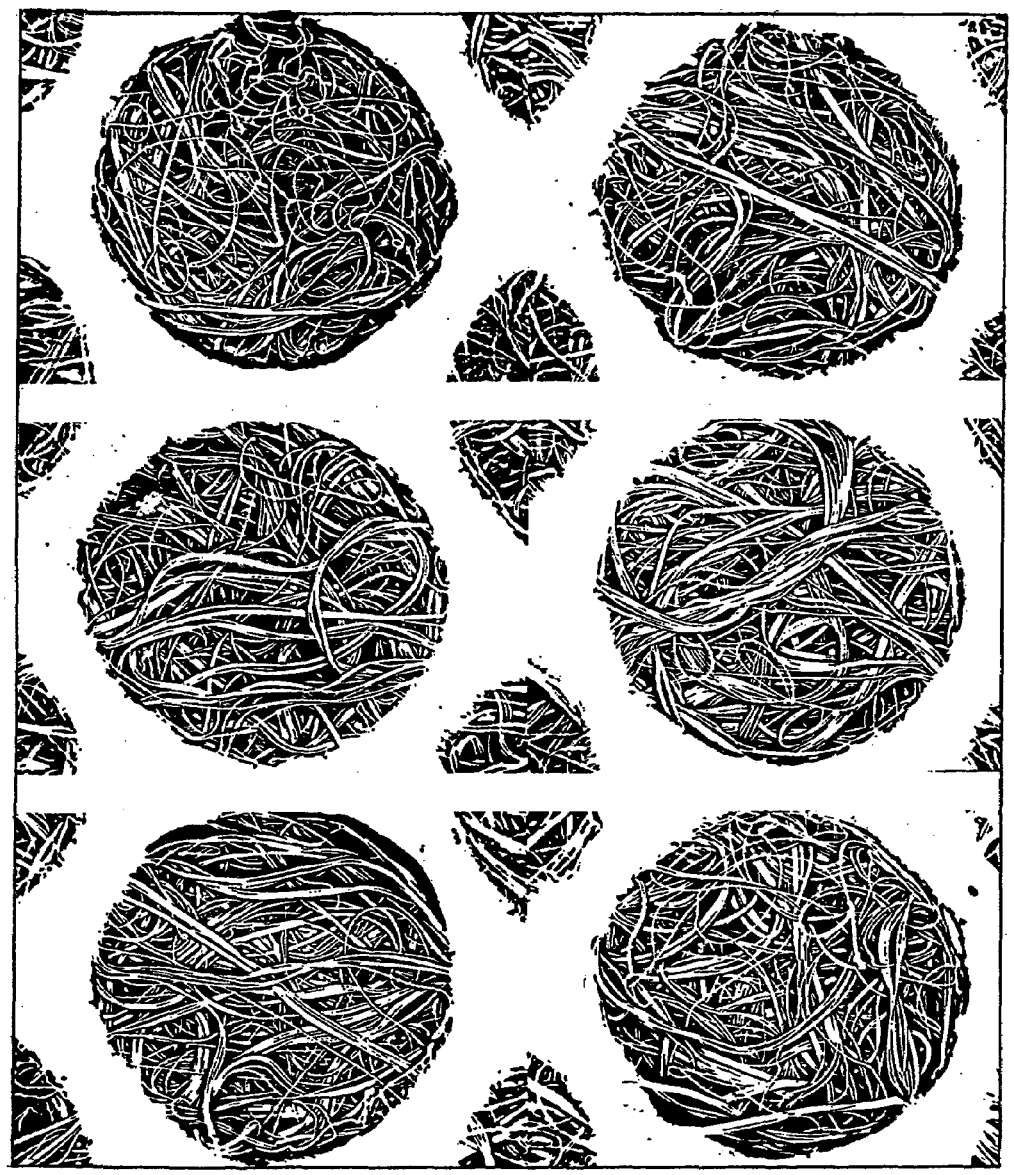
FIG. 17 is a BSE/HICON photomontage of a non-woven point unbonded material.

In another test, described as a back-scatter electron detection and TY 51 Hicontrast Polaroid® film (BSE/HICON) Surface Porosity test, 6 samples (½"×¾") of the spunbond and pub materials were taken from a 4"×6" section of material. The 6 samples were gold coated with a sputter coater. Using back-scatter electron detection, photomontages, shown in FIGS. 16 and 17, were prepared for each material at 20× magnification. The photomontages were analyzed, and data was obtained, using the QUANTIMET 970 Image Analsyis System, available from Leica Corp., located in Deerfield, Ill. In particular, the QUIPS CONWID routine, set forth at Appendix 1, was used for performing this work. The results of those tests are reported at Tables 2-9.

TABLE 2

DISTRIBUTION OF COUNT vs PERCAREA

Cambridge Instruments QUANTIMET 970 QUIPS/MX: V08.00 USER:
ROUTINE: CONWID
SPECIMEN: .6 OSY WW SB LAMINAT
Total PERCAREA = 972. Mean = 40.5 Std Dev = 3.65
Undersize Count + 0 Oversize Count = 0.

| PERCAREA (% AREA) LIMITS | COUNT | |
|---|---|---|
| 0.-6.00 | 0. | : |
| 6.00-12.00 | 0. | : |
| 12.00-18.00 | 0. | : |
| 18.00-24.00 | 0. | : |
| 24.00-30.00 | 0. | : |
| 30.00-36.00 | 2. | :**** |
| 36.00-42.00 | 14. | :**************************** |
| 42.00-48.00 | 8. | :***************** |
| 48.00-54.00 | 0. | : |
| 54.00-60.00 | 0. | : |
| 60.00-66.00 | 0. | : |
| 66.00-72.00 | 0. | : |
| 72.00-78.00 | 0. | : |
| 78.00-84.00 | 0. | : |
| 84.00-90.00 | 0. | : |

FIELD COUNT vs PERCENT AREA HISTOGRAM
AVE % AREA = 40.630

TABLE 3

DISTRIBUTION OF FEATURE1 COUNT vs CALC.C

Cambridge Instruments QUANTIMET 970 QUIPS : V08.00 USER:
ROUTINE : CONWID SPECIMEN : .6 OSY WW SB LAMINAT
Total FEATURE1 COUNT = 11064. Mean = 23.9 Std Dev = 11.2
Undersize Count = 0 Oversize Count = 0.

| CALC.C (MICRONS) LIMITS | COUNT (COUNT) | |
|---|---|---|
| 1.00-1.58 | 0. | : |
| 1.58-2.51 | 0. | : |
| 2.51-3.98 | 0. | : |
| 3.98-6.31 | 0. | : |
| 6.31-10.00 | 481 | :**** |
| 10.00-15.85 | 2575 | :************************* |
| 15.85-25.12 | 3690 | :************************************ |
| 25.12-39.81 | 3360 | :************************************ |
| 39.81-63.10 | 888 | :************ |
| 63.10-100.00 | 69 | : |
| 100.00-158.49 | 1 | : |
| 158.49-251.19 | 0. | : |
| 251.19-398.11 | 0. | : |
| 398.11-630.96 | 0. | : |
| 630.96-1000.00 | 0. | : |

PORE COUNT VS CON WIDTH (um)

TABLE 4

DISTRIBUTION OF FEATURE1 AREA vs CALC.C

Cambridge Instruments QUANTIMET 970 QUIPS: V08.00 USER:
ROUTINE : CONWID SPECIMEN : .6 OSY WW SB LAMINAT
Total FEATURE1 AREA = 36296340. Mean = 32.1 Std Dev = 11.9
Undersize Count = 0 Oversize Count = 0.

| CALC.C (MICRONS) LIMITS | AREA (SQ MICRONS) | |
|---|---|---|
| 100.-1.58 | 0. | : |
| 1.58-2.51 | 0. | : |
| 2.51-3.98 | 0. | : |
| 3.98-6.31 | 0. | : |
| 6.31-10.00 | 72203.47000 | : |
| 10.00-15.85 | 1240307.000 | :** |
| 15.85-25.12 | 9073056. | :****************** |
| 25.12-39.81 | 18701750. | :************************************ |
| 39.81-63.10 | 6430334.000 | :************ |
| 63.10-100.00 | 747591.8000 | : |
| 100.00-158.49 | 31182.57000 | : |
| 158.49-251.19 | 0. | : |
| 251.19-398.11 | 0. | : |
| 398.11-630.96 | 0. | : |
| 630.96-1000.00 | 0. | : |

CUM PORE A% VS CON WIDTH (um)

TABLE 5

DISTRIBUTION OF COUNT vs ANISOT

Cambridge Instruments QUANTIMET 970 QUIPS: V08.00 USER:
ROUTINE : CONWID SPECIMEN : .6 OSY WW SB LAMINAT
Total ANISOT = 18.4000 Mean = 0.767 Std Dev = 0.0917
Undersize Count + 0 Oversize Count = 0.

| ANISOT (UNITS) LIMITS | COUNT | |
|---|---|---|
| 0.-0.10 | 0. | : |
| 0.10-0.20 | 0. | : |

TABLE 5-continued

DISTRIBUTION OF COUNT vs ANISOT

| | | |
|---|---|---|
| 0.20-0.30 | 0. | : |
| 0.30-0.40 | 0. | : |
| 0.40-0.50 | 0. | : |
| 0.50-0.60 | 1. | :*** |
| 0.60-0.70 | 4. | :*************** |
| 0.70-0.80 | 10. | :**************************************** |
| 0.80-0.90 | 8. | :************************ |
| 0.90-1.00 | 1. | :*** |
| 1.00-1.10 | 0. | : |
| 1.10-1.20 | 0. | : |
| 1.20-1.30 | 0. | : |
| 1.30-1.40 | 0. | : |
| 1.40-1.50 | 0. | : |

% OF FIELDS vs ANISOTROPY
AVERAGE PORE ANISOTROPY (TAN THETA) = 0.77534
TOTAL SCANNED AREA = 0.52659 SQ CM

TABLE 6

DISTRIBUTION OF COUNT vs PERCAREA

Cambridge Instruments QUANTIMET 970 QUIPS/MX: V08.00 USER:
ROUTINE : CONWID SPECIMEN : 2.0 OSY PUB
Total PERCAREA = 978. Mean = 40.8 Std Dev = 7.18
Undersize Count = 0 Oversize Count = 0.

| PERCAREA (% AREA) LIMITS | COUNT | |
|---|---|---|
| 0.-6.00 | 0. | : |
| 6.00-12.00 | 0. | : |
| 12.00-18.00 | 0. | : |

TABLE 6-continued

DISTRIBUTION OF COUNT vs PERCAREA

| | | |
|---|---|---|
| 18.00-24.00 | 0. | : |
| 24.00-30.00 | 1. | :**** |
| 30.00-36.00 | 6. | :************************ |
| 36.00-42.00 | 6. | :************************ |
| 42.00-48.00 | 8. | :******************************** |
| 48.00-54.00 | 2. | :******** |
| 54.00-60.00 | 1. | :**** |
| 60.00-66.00 | 0. | : |

TABLE 6-continued

DISTRIBUTION OF COUNT vs PERCAREA

| | | |
|---|---|---|
| 66.00-72.00 | 0. | : |
| 72.00-78.00 | 0. | : |
| 78.00-84.00 | 0. | : |
| 84.00-90.00 | 0. | : |

FIELD COUNT vs PERCENT AREA HISTOGRAM
AVE%
AREA = 40.665

TABLE 7

DISTRIBUTION OF FEATURE1 COUNT vs CALC.C

Cambridge Instruments QUANTIMET 970 QUIPS/MX: V08.00 USER:
ROUTINE : CONWID SPECIMEN : 2.0 OSY PUB
Total FEATURE1 COUNT = 2147. Mean = 25.2 Std Dev = 17.3
Undersize Count = 0 Oversize Count = 0.

| CALC.C (MICRONS) LIMITS | COUNT | |
|---|---|---|
| 1.00-1.58 | 0. | : |
| 1.58-2.51 | 0. | : |
| 2.51-3.98 | 0. | : |
| 3.98-6.31 | 0. | : |
| 6.31-10.00 | 221. | :************ |
| 10.00-15.85 | 667. | :*************************************** |
| 15.85-25.12 | 421. | :********************* |
| 25.12-39.81 | 489. | :************************** |
| 39.81-63.10 | 267. | :************** |
| 63.10-100.00 | 73. | :*** |
| 100.00-158.49 | 8. | : |
| 158.49-251.19 | 1. | : |
| 251.19-398.11 | 0. | : |
| 398.11-630.96 | 0. | : |
| 630.96-1000.00 | 0. | : |

PORE COUNT VS CON WIDTH (um)

TABLE 8

DISTRIBUTION OF FEATURE1 AREA vs CALC.C

Cambridge Instruments QUANTIMET 970 QUIPS: V08.00 USER:
ROUTINE : CONWID SPECIMEN : 2.0 OSY PUB
Total FEATURE1 AREA= 40203880. Mean = 36.4 Std Dev = 15.7
Undersize Count = 0 Oversize Count = 0.

| CALC.C (MICRONS) LIMITS | AREA(SQ MICRONS) | |
|---|---|---|
| 1.00-1.58 | 0. | : |
| 1.58-2.51 | 0. | : |
| 2.51-3.98 | 0. | : |
| 3.98-6.31 | 0. | : |
| 6.31-10.00 | 49332.16000 | : |
| 10.00-15.85 | 578338.6000 | :* |
| 15.85-25.12 | 6682890. | :********* |
| 25.12-39.81 | 21962620. | :******************************** |
| 39.81-63.10 | 8517650. | :************ |
| 63.10-100.00 | 2113692.000 | :*** |
| 100.00-158.49 | 257262.8000 | : |
| 158.49-251.19 | 42126.75000 | : |
| 251.19-398.11 | 0. | : |

TABLE 8-continued

DISTRIBUTION OF FEATURE1 AREA vs CALC.C

| | | |
|---|---|---|
| 398.11-630.96 | 0. | : |
| 630.96-1000.00 | 0. | : |
| CUM PORE A % VS CON WIDTH (um) | | |

TABLE 9

DISTRIBUTION OF COUNT vs ANISOT

Cambridge Instruments QUANTIMET 970 QUIPS: V08.00 USER: ROUTINE : CONWID SPECIMEN : 2.0 OSY PUB
Total ANISOT = 26.5500 Mean = 1.15 Std Dev = 0.212
Undersize Count + 0 Oversize Count = 1.

| ANISOT (UNITS) LIMITS | COUNT | |
|---|---|---|
| 0.-0.10 | 0. | : |
| 0.10-0.20 | 0. | : |
| 0.20-0.30 | 0. | : |
| 0.30-0.40 | 0. | : |
| 0.40-0.50 | 0. | : |
| 0.50-0.60 | 0. | : |
| 0.60-0.70 | 1. | :******** |
| 0.70-0.80 | 0. | : |
| 0.80-0.90 | 2. | :***************** |
| 0.90-1.00 | 2. | :***************** |
| 1.00-1.10 | 3. | :************************* |
| 1.10-1.20 | 5. | :****************************************** |
| 1.20-1.30 | 5. | :****************************************** |
| 1.30-1.40 | 1. | :******** |
| 1.40-1.50 | 4. | :****************************** |

OF FIELDS vs ANISOTROPY
AVERAGE PORE ANISOTROPY (TAN THETA) = 1.171
TOTAL SCANNED AREA = 0.52659 SQ CM

The convoluted width (Conwid) of a pore in the nonwoven material, analyzed using the CONWID routine, is the average width of a pore independent of the convolution, shape, orientation or protrusion of the fibers or other element defining the pore. The CONWID routine provides analysis and data, including histograms, on the number of pores, and the average coverage (%A) and pore-wide data, both count and area-weighted. For example, in comparing Tables 2 and 6, it can be seen that the spunbond laminate material has a similar average % area as the PUB material, but that the PUB material has a greater standard deviation. In comparing Tables 3 and 7, it can be seen that the spunbond laminate material has much greater total pore count (11064) versus the PUB material (2147), and with only a slightly smaller average pore size. In comparing Tables 4 and 8, it can be seen that the spundbond laminate material has a slightly lesser total pore area than the PUB material. Finally, Tables 5 and 9 compare the anisotropic properties of the spunbond laminate material and the PUB material, where it can be observed that the PUB material has a greater mean anisotropy than the spunbond laminate material.

As shown in Tables 10 and 11, a fuzz-on-edge test, which is an image analysis test, was also used to analyze the spunbond laminate material versus the PUB material. The fuzz-on-edge test measures the intensity of protruding fiber loft in perimeter length per unit-edge length.

The image analysis data are taken from two glass plates made into one fixture. Each plate has a sample folded over the edge with the sample folded in the CD direction and placed over the glass plate. The edge is beveled to $1/16$" thickness. The testing method and equipment is further described and disclosed in U.S. Provisional Application No. 60/204,083, filed May 12, 2000, the entire disclosure of which is hereby incorporated herein by reference. For example, in one sequence, the glass plates have a thickness of $1/4$ inch, each having a beveled edge with a thickness of $1/16$ inch. During the testing, samples are placed over the beveled edges. Multiple images of the folded edges are then taken along the edge. Thirty (30) files of view are examined on each folded edge to provide a total of sixty (60) files of view. Each edge is about 6.5 mm in height. Each view has a Fuzz-On-Edge)FOE) or "PR/EL" value measured before and after removal of protruding fibers. PR/EL is the perimeter per edge-length examined in each filed of view. In particular, PR is the perimeter around the protruding fibers, and EL is the length of the measure sample. The PR/EL values are averaged and assembled into a histogram, shown in Tables 10 and 11. The analysis is completed and the data obtained using the QUANTIMET 970 Image Analysis System described above using standard conditions with a 60-mm Micro-Mikkor lens. The QUIPS routine for performing this work is designated as FUZZ10, and is set forth at Appendix 2.

TABLE 10

DISTRIBUTION OF COUNT vs PROVEREL

Cambridge Instruments QUANTIMET 970 QUIPS: V08.02 USER: ROUTINE : FUZZIO SPECIMEN : .6 OSY WW SB LAMINAT
AVE PR-OVER-EL (UM/UM) = 0.36932
TOTAL NUMBER OF FIELDS = 60.
FIELD HEIGHT (HM) = 6.087
Total PROVEREL = 22.5000 Mean = 0.375 Std Dev = 0.460
Undersize Count = 0. Oversize Count = 0.

| PROVEREL (HM/MH) LIMITS | COUNT | |
|---|---|---|
| 0.-0.25 | 35. | :****************************** |
| 0.25-0.50 | 14. | :********************* |
| 0.50-0.75 | 4. | :**** |
| 0.75-1.00 | 1. | :* |
| 1.00-1.25 | 2. | :** |
| 1.25-1.50 | 1. | :* |
| 1.50-1.75 | 1. | :* |
| 1.75-2.00 | 0. | : |
| 2.00-2.25 | 2. | :** |
| 2.25-2.50 | 0. | : |
| 2.50-2.75 | 0. | : |
| 2.75-3.00 | 0. | : |
| 3.00-3.25 | 0. | : |
| 3.25-3.50 | 0. | : |
| 3.50-3.75 | 0. | : |
| 3.75-4.00 | 0. | : |
| 4.00-4.25 | 0. | : |
| 4.25-4.50 | 0. | : |

TABLE 10-continued

DISTRIBUTION OF COUNT vs PROVEREL

| | | |
|---|---|---|
| 4.50-4.75 | 0. | : |
| 4.75-5.00 | 0. | : |

TABLE 11

DISTRIBUTION OF COUNT vs PROVEREL

Cambridge Instruments QUANTIMET 970 QUIPS: V08.02 USER
ROUTINE : FUZZIO SPECIMEN : 2.0 OSY PUB
AVE PR-OVER-EL (UM/UM) = 0.92355
TOTAL NUMBER OF FIELDS = 60.
FIELD HEIGHT (HM) = 6.087
Total PROVEREL = 55.500 Mean = 0.925 Std Dev = 0.614
Undersize Count = 0. Oversize Count = 0.

| PROVEREL (HM/MH) LIMITS | COUNT | |
|---|---|---|
| 0.-0.25 | 5. | :************* |
| 0.25-0.50 | 9. | :************************* |
| 0.50-0.75 | 11. | :******************************* |
| 0.75-1.00 | 15. | :******************************************* |
| 1.00-1.25 | 4. | :************ |
| 1.25-1.50 | 11. | :******************************* |
| 1.50-1.75 | 1. | :** |
| 1.75-2.00 | 1. | :** |
| 2.00-2.25 | 0. | : |
| 2.25-2.50 | 2. | :****** |
| 2.50-2.75 | 0. | : |
| 2.75-3.00 | 0. | : |
| 3.00-3.25 | 0. | : |
| 3.25-3.50 | 0. | : |
| 3.50-3.75 | 1. | :** |
| 3.75-4.00 | 0. | : |
| 4.00-4.25 | 0. | : |
| 4.25-4.50 | 0. | : |
| 4.50-4.75 | 0. | : |
| 4.75-5.00 | 0. | : |

As can be seen when comparing Tables 10 and 11, the average PR/EL (0.37) for the spunbond laminate material is less than the PR/EL average (0.92) for the PUB material. Likewise, the total PR/EL (22.5) for the spunbond laminate was less than the total PR/EL (55.5) for the PUB material. Preferably, the non-woven material used for the body panels will have an average PR/EL less than 0.75, more preferably less than 0.60 and even more preferably less than 0.50. Preferably, the non-woven material used for the body panels will have an total PR/EL less than 50.0, more preferably less than 35.0 and even more preferably less than 25.0.

Referring to FIGS. 1-3, fastening members or tabs 42 are attached and extend laterally inboard from the outboard side edge 24 of the front body panel 4 from an attachment location 45. The front body panel 4 includes a middle portion 33, or landing member, and opposite side portions 35. Opposite longitudinally extending lines of weakness 37 separate the middle, landing member portion from the opposite side portions, such that the side portions are initially breakably attached to opposite sides of the landing member portion. The lines of weakness 37 can comprise a perforation or other series of cuts that allow a user or the manufacturer to separate the side portions from the middle portion. For example, the absorbent garment can be broken after the garment is applied to a user, or beforehand. Preferably, the fastening members 42 are secured to the garment-side surface of the side portions 35 between the side edge 24 of the front body panel and the line of weakness 35.

It should be understood that in other embodiments the fastening members can be secured to the rear body panel and engage the front body panel or, conversely, can be secured to the front body panel and engage the rear body panel, preferably along at least a portion that is not elasticized. Preferably, the fastening members are fixedly secured to the outer, garment-side surface of the front and/or rear body panels, and releasably engage the outer, garment-side surface of the front and/or rear body panels, although it should be understood that the fastening members could be fixedly secured to an inner body-side surface of front and/or rear body panels and releasably engage an inner, body-side surface of the front and/or rear body panels.

The opposite side edges 24 of the front body panel 4 are joined to the opposite side edges 28 of the rear body panel 6 to form a seam 39, which has a longitudinal length (SSL), which may be the same as or less than the lengths (FPL) and (RPL) of either of the front and rear body panels. In this way, prior to the breaking of the line of weakness 37, the absorbent garment can be configured as a pant-like garment, which can be pulled over the legs of the user. After the garment is applied to the user, the lines of weakness can be broken, if desired, or left intact, as the fasteners are adjusted to fit the garment to the user. If desired, the lines of weakness can be broken prior to securing the garment to the user, for example when the user is bed-ridden. In this configuration, the garment is laid beneath the user and is secured to the user with the fastening tabs. By providing the side portions, and by connecting the fastening tabs to the front panel, instead of the rear body panel, the tabs are located at the front of the user so as to not provide discomfort to the user when lying on their backs and to allow the fasteners to be more easily seen and adjusted by the user.

It should be understood that the front and rear body panels can be made as a unitary member that extends along the crotch from the front to back and with the sides thereof connected to form side seams. Alternatively, the front and rear body panels can be formed integrally, for example as one panel extending around the waist and hips of the user.

Preferably, as shown in FIGS. 1-3, 10 and 11, the fastening members 42 comprise a carrier member 43 that is formed in a generally side-ways, "U" shape, with a vertical extending base member 55 and a pair of laterally extending and longitudinally spaced tab members 47. The carrier member could also comprise one or more than two tab members. The carrier members are preferably fixedly secured to the side portions of the body panel 4 with adhesive bonds 49, sonic bonds, thermal bonds, pinning, stitching or other known types of attachment, as shown for example in FIGS. 2-6 and 11. In alternative embodiments, the fastening members can be fixedly secured to the rear panel, as shown in FIG. 9, or to one or both of the front and rear panels, e.g., at the seam, as shown for example in FIG. 10.

Each carrier member 43 has a longitudinal length (TL). Each of the tab members 47 comprises an engagement portion having a longitudinal length (FTL), as shown in FIGS. 10 and 11. The combined longitudinal length of the engagement portions of the two tab members is the defined as an engagement length (ET). For example, in the embodiments shown in FIGS. 9-11, ET=FTL1+FTL2. The engagement portion preferably comprises an array of hooks, as explained below, but alternatively can comprise various adhesives, such as pressure sensitive adhesives, buttons, zippers and other releasable and reattachable fastening devices.

In one embodiment, shown in FIG. 9, each fastening member 42 is comprised of two separate, longitudinally spaced tab members 47, each having a length (TTL) and an engagement portion having a length (FTL), with TTL preferably being substantially the same as FTL. The length of the fastening member (TL) is defined as the sum of length of the tab members (TTL), and the engagement length (ET) is equal to the sum of the lengths of the engagement portions FTL.

In any of the embodiments, the two or more tab members provides a pant like fit that controls the waist and leg openings in the front and back of the garment, and also allows the user to adjust the fit of the garment without totally undoing the garment. For example, the user can release one of the tab members and refasten it without undoing the other tab member.

Referring to FIGS. 9-11, the preferred ratio of the engagement length ET to the front panel length FPL is at least about 20%, and more preferably the engagement length ET is at least about 30% of the front panel length FPL, and most preferably is at least about 40% of the front panel length. Preferably the engagement length ET is less than about 90% of the front panel length FPL, and more preferably the engagement length ET is less than about 80% of the front panel length FPL, and most preferably is less than about 60% of the front panel length.

In addition, the fastener length TL is preferably at least about 50% of the side seam length SSL, and more preferably is at least about 70% of the side seam length SSL and most preferably is at least about 90% of the side seam length. The fastener length TL is also preferably at least about 50% of the front panel length FPL, and more preferably is at least about 70% of the front panel length FPL, and most preferably is at least about 90% of the front panel length FPL. Likewise, the fastener length TL is preferably at least about 50% of the length of the outboard edge of the rear body panel RPL, and more preferably is at least about 70% of the length of the outboard edge of the rear body panel RPL, and most preferably is at least about 90% of the length of the outboard edge of the rear body panel RPL.

A hook-type fastener member 51, or hook strip, is secured to the carrier member 43 with adhesive, ultrasonic bonding, stitching or other known attachment devices. The end portion 53 or tip of the carrier member can be left uncovered by the fastener member 51, such that it can be lifted or flexed and grasped by a user as they disengage or peel back the fastener member. It should be understood that the term "hook" as used herein means any element capable of engaging another element, and is not intended to limit the form of the engaging elements, for example to include only "hooks," but rather encompasses any form shape of engaging element, whether unidirectional or bi-directional. Various hook configurations are described in U.S. Pat. No. 5,845,375 to Miller et al., U.S. Pat. No. 6,132,660 to Kampfer, U.S. Pat. No. 6,000,106 to Kampfer, U.S. Pat. No. 5,868,987 to Kampfer, U.S. Pat. No. 4,894,060 to Nestegard, and U.S. Pat. No. 6,190,594 B1 to Gorman, the entire disclosures of which are incorporated by reference herein. Some examples of hook fasteners are the various CS600 hook fasteners, including the XKH-01-002 CS600, 2300 Pin Density hook fastener (Part No. XKH-01-002/60MM/SP#2628), manufactured by Minnesota Mining and Manufacturing Co., St. Paul Minn.

In one preferred embodiment, a mushroom-type hook strip comprises a homogeneous backing 57 of thermoplastic resin and, integral with backing, an array 59 of upstanding stems 61 distributed across at least one face of the backing, each having a mushroom head 63. The array of hooks on each strip comprise an engagement portion having a longitudinal length (FTL). The stems can have a molecular orientation as evidenced by a birefringence value of at least 0.001, and the mushroom heads having circular disc shapes with generally planar end surfaces opposite the backing, which disc shaped heads preferably have diameter to thickness ratios of greater than about 1.5 to 1.

The stems 61 of the hook strip can be molecularly orientated as evidenced by a birefringence value of at least 0.001. As such, they have significantly greater stiffness and durability, as well as greater tensile and flexural strength, than would be achievable without such orientation. Because of these qualities, the portions of the stems not heated by a heating surface during the forming process remain resiliently flexible during a deforming step, which preferably involves the application of heat to the stem tips by contact with the heated surface of a metal roller. Such contact forms the tip of each stem into a circular disc shaped mushroom head at the tip of each stem, which head has a substantially flat inner surface that enhances its holding power when engaged with a loop.

As compared to hook strips that have unoriented stems, the enhanced strength of the hooks of the hook strip makes them less likely to break during disengagement. When the hook strip is used with the non-woven material herein described, the enhanced strength of the hooks makes them less likely to break under disengagement forces than the fibers of the material, a beneficial attribute for at least two reasons. First, broken hooks can create debris whereas a broken fiber typically does not. Furthermore, the non-woven material typically contains many more engageable fibers than there are hooks per unit area, thus allowing a greater number of disengagements before a hook-and-loop fastener becomes useless.

Although the stems of the hook strip preferably are generally circular in cross section, other suitable cross sections include rectangular and hexagonal. The stems preferably have fillets at their bases, both to enhance strength and stiffness and for easy release from a mold in which they are formed. In addition, the stems can be tapered, preferably from a larger to a smaller cross-section as one moves from the base to the head.

The stem portions are preferably at an angle of about 90 degrees from the backing substrate, however, this angle can range from about 80 to about 100 degrees, preferably 85 to about 95 degrees. The hook head portion is formed on the distal end of the stem. The hook head can be elongated in on or more directions forming the fiber engaging portions. These fiber engaging portions extend outward from the stem portion at any angle so that they can project upwardly away from the film backing, parallel with the film backing or even downward toward the film backing.

Figure 8:
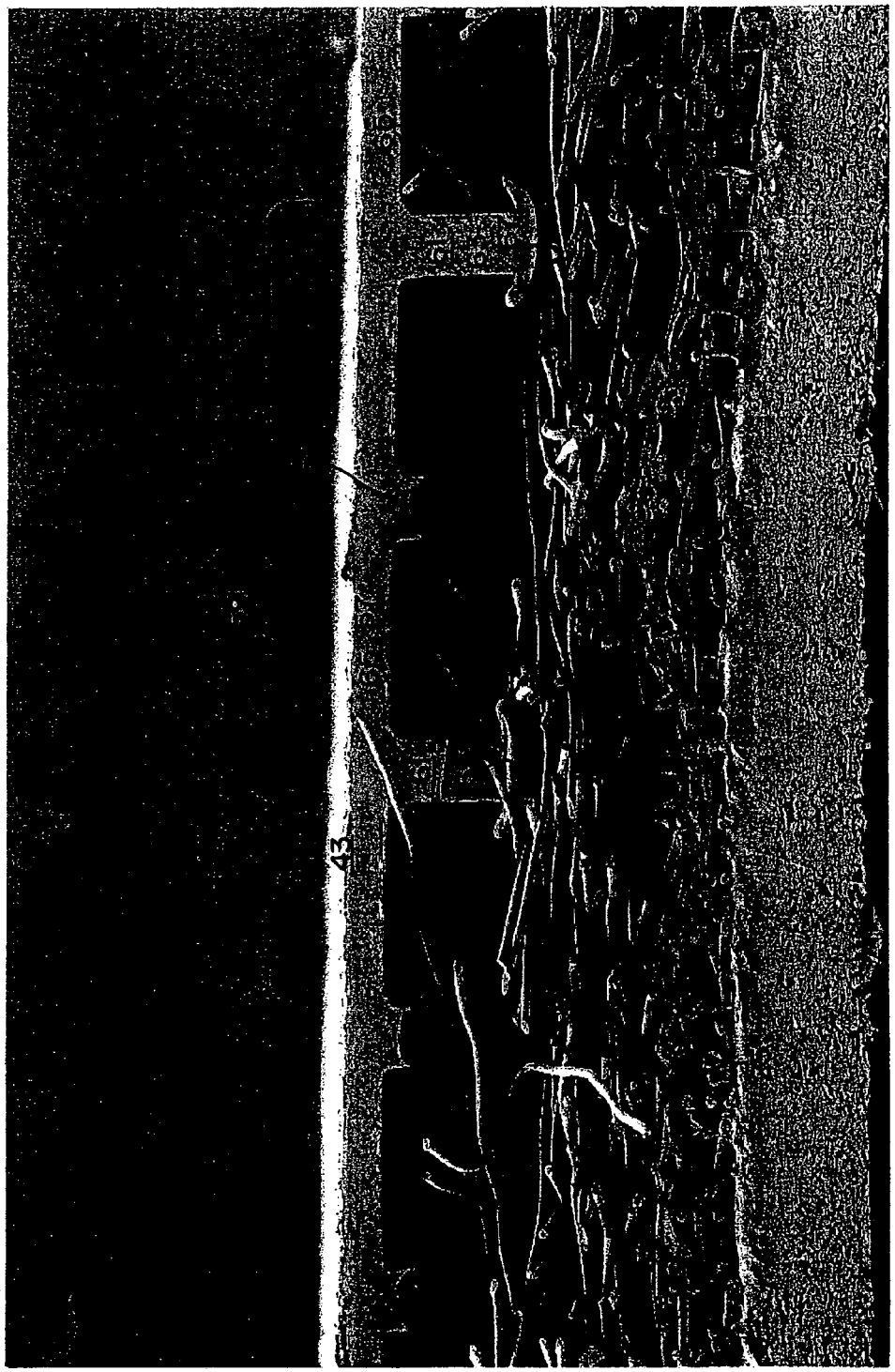
FIG. 8 is an enlarged side cross-sectional view of a hook-type fastener engaging the front body panel material.

For example, as shown in FIG. 8, the hook head portion has a deformed fiber engaging portion that projects downward. Preferably, the lower surface of the fiber engaging portion also projects downward form a crook between the lower face of the fiber engaging portion and the stem base portion. In one preferred embodiment, the heads of the hooks generally project at a downward angle from the hook head top portions toward the base. This downward angle (measured from a reference line taken from the top of the hook head and parallel with the backing) is generally from about 0 to about 70 degrees, preferably from about 5 to about 60 degrees and most preferably from about 5 to about 35 degrees (defined by a linear extent running from a center region of the hook head top portion to an end of the hook head fiber engaging portion).

The head shape with its high diameter to thickness ratio, and the small size and close spacing or high density of individual hooks that are provided by the hook strip according to the present invention makes it able to easily firmly releasably engage non-woven materials in shear, possibly because the many thin heads can easily move radially into engagement with rather small fibers. Thus the hook strip is particularly useful for hook-and-loop fastening when the "loops" are provided by non-woven materials which are not particularly adapted for use as the loop portions of hook and loop fasteners, and which are not as well engaged by known prior art hook strips. For example, the hook strip is particularly well-suited for engaging the topographically flatter non-woven materials described above, including the non-woven spunbond material, which has relatively fewer loose, outwardly extending, free fibers than conventional loop materials, but still provides a relatively high number of pores, of sufficient size, such that the material can be engaged by the hooks. Indeed, once the hooks are received in the pores, or embedded in the non-woven material, the fastening tabs provide excellent shear characteristics, such that the garment is securely fastened during normal wearing conditions.

In general, the hooks are of uniform height, preferably of from about 0.10 to 1.30 mm in height, and more preferably from about 0.18 to 0.51 mm in height; have a density on the backing preferably of from 60 to 1,600 hooks per square centimeter, and more preferably from 125 to 690 hooks per square centimeter, and preferably greater than about 150 hooks per square centimeter; have a stem diameter adjacent the heads of the hooks preferably of from 0.07 to 0.7 mm, and more preferably from about 0.1 to 0.3 mm. The deformed hook heads project radially past the stems on at least one side preferably by an average of about 0.01 to 0.3 mm, and more preferably by an average of about 0.02 to 0.25 mm and have average thicknesses between their outer and inner surfaces (i.e., measured in a direction parallel to the axis of the stems) preferably of from about 0.01 to 0.3 mm and more preferably of from about 0.02 mm to 0.1 mm. The hook heads have average head diameter (i.e., measured radially of the axis of the heads and stems) to average head thickness ratio preferably of from 1.5:1 to 12:1, and more preferably from 2.5:1 to 6:1.

For most hook-and-loop uses, the hooks of the hook strip should be distributed substantially uniformly over the entire area of the hook strip, usually in a square or hexagonal array.

To have both good flexibility and strength, the backing of the hook strip preferably is from 0.02 to 0.5 mm thick, and more preferably is from 0.06 to 0.3 mm in thick, especially when the hook strip is made of polypropylene or a copolymer of polypropylene and polyethylene. For some uses, a stiffer backing could be used, or the backing can be coated with a layer of pressure sensitive adhesive on its surfaces opposite the hooks by which the backing could be adhered to a substrate, such as the carrier member 43, so that the backing could then rely on the strength of the substrate to help anchor the hooks.

Virtually any orientable thermoplastic resin that is suitable for extrusion molding may be used to produce the hook strip. Thermoplastic resins that can be extrusion molded and should be useful include polyesters such as poly(ethylene terephthalate), polyamides such as nylon, poly(styrene-acrylonitrile), poly(acrylonitrile-butadiene-styrene), polyolefins such as polypropylene, and plasticized polyvinyl chloride. One preferred thermoplastic resin is a random copolymer of polypropylene and polyethylene containing 17.5% polyethylene and having a melt flow index of 30, that is available as SRD7-463 from Shell Oil Company, Houston, Tex.

Referring to FIG. 8, the hook strip is shown as having a substantially continuous planar backing 57 of thermoplastic resin. Integral with the backing is an array 59 of hooks 65 projecting generally at right angles to one major surface of the backing. Each of the hooks 65 has a stem 61, and, at the end of the stem opposite the backing, a generally circular plate-like cap or head projecting radially past or overhanging the stem so as to form a fiber engaging portion 63 that projects downward. Preferably, the lower surface of the fiber engaging portion 63 also projects downward form a crook between the lower face of the fiber engaging portion and the stem base portion. The stem 61 can also have a fillet around its base.

When the absorbent garment is secured to the user, the fastening tabs 42 secured to the side portions of the front body panels 4 releasably engage or are otherwise connected to the middle landing member portion of the body panels 4. Preferably, at least a portion of the array of hooks 65 engage the non-elasticized area of the middle portion. In particular, the heads on the hooks engage the fibers in the non-woven spunbond material without the need to provide additional loops or otherwise alter the material. It should be understood however, that a portion of the array of hooks 65 can engage the elasticized areas. For example, a portion of the array of hooks on the upper tab member may engage a portion of the elasticized area along the waist portion of the front panel, while a portion of the hooks on the lower tab member may engage a portion of the elasticized area along the leg opening of the garment. The landing member portion of the front body panel member can also be configured with an additional material, or landing patch, secured to the garment side thereof and which comprises a loop material.

Referring again to FIGS. 1-4, the absorbent garment includes an absorbent composite 50 having first and second longitudinally opposed terminal end edges 60, 62. The absorbent composite includes a substantially liquid permeable topsheet 64, or liner, and a substantially liquid impermeable backsheet 68, or outer cover. A retention portion 70 is disposed or sandwiched between the topsheet and the backsheet, which are connected. The topsheet, backsheet and other components of the absorbent composite 50 can be joined for example with adhesive bonds 77, sonic bonds, thermal bonds, pinning, stitching or any other attachment techniques known in the art, as well as combinations thereof. For example, a uniform continuous layer of adhesive, a patterned layer of adhesive, a sprayed pattern of adhesive or any array of lines, swirls or spots of construction bonds may be used to join the topsheet and backsheet, or any of the other components described herein.

Additional layers, including for example, a surge layer 72, are also preferably incorporated into the absorbent composite. Preferably, the surge layer does not run the entire length of the absorbent composite and is shorter than the retention portion. The topsheet can be indirectly joined to the backsheet by affixing the topsheet to intermediate layers, such as the surge layer or retention portion, which in turn is affixed to the backsheet.

The backsheet 68 is preferably liquid impermeable, but may be liquid permeable, e.g., when an additional barrier layer is used with the retention portion. For example, in one embodiment, the backsheet can be made from a thin plastic film, or other flexible, substantially liquid-impermeable material. As used herein, the term "flexible" means a material that is compliant and which will readily conform to the general shape and contour of the body of the user. The backsheet prevents various bodily fluids and exudates from wetting or otherwise contaminating various bedding or outer garments worn by the user over the absorbent garment. In particular, the backsheet can include a film, such as a polyethylene film, having a thickness of from about 0.012 mm to about 0.051 mm.

In various constructions, the topsheet can comprise various woven or nonwoven materials. For example, the topsheet can be composed of a meltblown or spunbonded web of desired fibers, and may also be a bonded-carded web. For example, the topsheet can be made of a substantially hydrophobic material, and the hydrophobic material may optionally be treated with a surfactant or otherwise processed to import a desired level of wettability and hydrophilicity. In one particular embodiment of the invention, the topsheet is a nonwoven, spunbond polypropylene fabric composed of about 2.8-3.2 denier fibers formed into a web having a basis weight of about 22 gsm and density of about 0.06 gm/cc. The fabric can be surface treated with an operative amount of surfactant, such as about 0.28% Triton X-102 surfactant. The surfactant can be applied by any conventional means, such as spraying, printing, brush coating or the like.

In various constructions, the backsheet can comprise a woven or nonwoven fibrous web layer, which is treated or constructed, partially or wholly, to impart the desired levels of liquid impermeability to selected regions that are adjacent to or proximate the absorbent retention portion. For example, the backsheet may include a gas-permeable, nonwoven fabric layer laminated to a polymer film layer which may or may not be gas-permeable. Other examples of fibrous, cloth-like backsheet materials can comprise a stretch thinned or stretch thermal laminate material composed of a 0.6 mil (0.015 mm) thick polypropylene cast film and a 0.7 ounce per square yard (23.8 gsm) polypropylene spunbond material (2 denier fibers). A material of this type has been employed to form the outercover of a HUGGIES® Ultratrim Disposable Diaper, which has been commercially available from Kimberly-Clark Corporation. The backsheet 68 typically provides the outercover of the article. Optionally, however, the article may include a separate outercover component member which is additional to the backsheet. The outercover can be joined, for example, to one or more of the absorbent composite and/or body panels.

The backsheet may include a micro-porous, "breathable" material which permits gases, such as water vapor, to escape from the absorbent garment while substantially preventing liquid exudates from passing through the backsheet. For example, the breathable backsheet may be composed of a microporous polymer film or a nonwoven fabric which has been coated or otherwise modified to impart a desired level of liquid impermeability. For example, a suitable microporous film can be a PMP-1 material, which is available from Mitsui Toatsu Chemicals, Inc., a company having offices in Tokyo, Japan; or an XKO-8044 polyolefin film available from 3M Company of Minneapolis, Minn. The backsheet may also be embossed or otherwise provided with a pattern or matte finish to exhibit a more aesthetically pleasing appearance.

In various configurations of the invention, where a component, such as the backsheet is configured to be permeable to gas while having a resistance and limited permeability to aqueous liquid, the liquid resistant component can have a construction which is capable of supporting a selected hydrohead of water substantially without leakage therethrough. A suitable technique for determining the resistance of a material to liquid penetration is Federal Test Method Standard FTMS 191 Method 5514, 1978, or an equivalent thereof. In one preferred embodiment, the backsheet is sufficiently impermeable to liquid and semi-liquid materials to substantially prevent the undesired leakage of waste materials, defined as exudates, including for example urine and feces. For example, the backsheet member can desirably support a hydrohead of at least about 45 centimeters (cm) substantially without leakage. The backsheet member can alternatively support a hydrohead of at least about 55 cm, and optionally, can support a hydrohead of at least about 60 cm, or more, to provide improved benefits.

The backsheet also can be extensible. In one preferred embodiment, the backsheet is capable of providing an elongation of at least about 1 cm when subjected to a tensile force of 11.8 g/cm, and further provides a substantially permanent deformation of at least about 20% when subjected to a tensile force of 19.70 g/cm and is then allowed to relax under a zero applied stress for a period of 1 minute.

For example, the extensible backsheet can be composed of a necked fiber, a creped fiber, a micro-pleated fiber, polymer films or the like, as well as combinations thereof. The fabrics may be woven or nonwoven materials, such as spunbond fabrics. One example of a suitable extensible material is a 60% necked, polypropylene spunbond having a basis weight of about 1.2 osy.

The backsheet also can be expandable, for example when it has one or more folds, e.g., one or more z-folds (not shown), or can be both extensible and expandable. The term expandable as used herein means to enlarge or to increase the extent or area, lateral and/or longitudinal, thereof, e.g., by unfolding one or more folds.

The retention portion 70 is preferably made of an absorbent material, which tends to swell or expand as it absorbs liquid excreted or exuded by the user. For example, the absorbent material can be made of airformed, airlaid and/or wetlaid composites of fibers and high absorbency materials, referred to as superabsorbents. Superabsorbents typically are made of polyacrylic acids, such as FAVOR 880 available from Stockhausen, Inc. of Greensboro, N.C. The fibers can be fluff pulp materials, such as Alliance CR-1654, or any combination of crosslinked pulps, hardwood, softwood, and synthetic fibers. Airlaid and wetlaid structures typically include binding agents, which are used to stabilize the structure. In addition, various foams, absorbent films, and superabsorbent fabrics can be used as an absorbent material.

In one preferred embodiment, an absorbent material is made of fibrous absorbent materials with a relatively high internal integrity, including for example one made with thermoplastic binder fibers in airlaid absorbents, e.g., pulp, bicomponent binding fibers, and superabsorbents, which have higher densities in the folded regions. The higher density and resulting smaller capillary size in these regions promotes better wicking of the liquid. Better wicking, in turn, promotes higher utilization of the absorbent material and tends to result in more uniform swelling throughout the absorbent material as it absorbs the liquid.

Various types of wettable, hydrophilic fibrous material can be used to form the component parts of absorbent, and particularly the retention portion 70. Examples of suitable fibers include naturally occurring organic fibers composed of intrinsically wettable material, such as cellulosic fibers; synthetic fibers composed of cellulose or cellulose derivatives, such as rayon fibers; inorganic fibers composed of an inherently wettable material, such as glass fibers; synthetic fibers made from inherently wettable thermoplastic polymers, such as particular polyester or polyamide fibers; and synthetic fibers composed of a nonwettable thermoplastic polymer, such as polypropylene fibers, which have been hydrophilized by appropriate means. The fibers may be hydrophilized, for example, by treatment with silica, treatment with a material which has a suitable hydrophilic moiety and is not readily removable from the fiber, or by sheathing the nonwettable, hydrophobic fiber with a hydrophilic polymer during or after the formation of the fiber. For the purposes of the present invention, it is contemplated that selected blends of the various types of fibers mentioned above may also be employed.

As used herein, the term "hydrophilic" describes fibers or the surfaces of fibers which are wetted by the aqueous liquids in contact with the fibers. The degree of wetting of the materials can, in turn, be described in terms of the contact angles and the surface tensions of the liquids and materials involved. Equipment and techniques suitable for measuring the wettability of particular fiber materials or blends of fiber materials can be provided by a Cahn SFA-222 Surface Force Analyzer System, or a substantially equivalent system. When measured with such system, fibers having contact angles less than 90° are designated "wettable", while fibers having contact angles greater than 90° are designated "nonwettable".

In particular arrangements, the retention portion of the absorbent may comprise a mixture of superabsorbent hydrogel-forming particles and synthetic polymer meltblown fibers, or a mixture of superabsorbent particles with a fibrous coform material comprising a blend of natural fibers and/or synthetic polymer fibers. The superabsorbent particles may be substantially homogeneously mixed with the hydrophilic fibers, or may be nonuniformly mixed. For example, the concentrations of superabsorbent particles may be arranged in a non-step-wise gradient through a substantial portion of the thickness (z-direction) of the absorbent structure, with lower concentrations toward the bodyside of the absorbent composite and relatively higher concentrations toward the outerside of the absorbent structure. Suitable z-gradient configurations are described in U.S. Pat. No. 4,699,823 issued Oct. 13, 1987 to Kellenberger et al., the entire disclosure of which is incorporated herein by reference in a manner that is consistent (not in conflict) with the present description. Alternatively, the concentrations of superabsorbent particles may be arranged in a non-step-wise gradient, through a substantial portion of the thickness (z-direction) of the absorbent structure, with higher concentrations toward the bodyside of the absorbent composite and relatively lower concentrations toward the outside of the absorbent structure. The superabsorbent particles may also be arranged in a generally discrete layer within the matrix of hydrophilic fibers. In addition, two or more different types of superabsorbent may be selectively positioned at different locations within or along the fiber matrix.

The high-absorbency material may comprise absorbent gelling materials, such as superabsorbents. Absorbent gelling materials can be natural, synthetic and modified natural polymers and materials. In addition, the absorbent gelling materials can be inorganic materials, such as silica gels, or organic compounds such as cross-linked polymers. The term "cross-linked" refers to any means for effectively rendering normally water-soluble materials substantially water insoluble but swellable. Such means can include, for example, physical entanglement, crystalline domains, covalent bods, ionic complexes and associations, hydrophilic associations, such as hydrogen bonding, and hydrophobic associations or Van der Walls forces.

Examples of synthetic absorbent gelling material polymers include the alkali metal and ammonium salts of poly (acrylic acid) and poly(methacrylic acid), poly(acrylamides), poly(vinyl ethers), maleic anhydride copolymers with vinyl ethers and alpha-olefins, poly(vinyl pyrrolidone), poly(vinylmorpholinone), poly(vingyl alcohol), and mixtures and copolymers thereof. Further polymers suitable for use in the absorbent composite include natural and modified natural polymers, such as hydrolyzed acrylonitrile-grafted starch, acrylic acid grafted starch, methyl cellulose, chitosan, carboxymethyl cellulose, hydroxypropyl cellulose, and the natural gums, such as alginates, xanthan gum, locust bean gum and the like. Mixtures of natural and wholly or partially synthetic absorbent polymers can also be useful in the present invention. Other suitable absorbent gelling materials are disclosed by Assarsson et al. in U.S. Pat. No. 3,901,236 issued Aug. 26, 1975, which is hereby incorporated herein by reference. Processes for preparing synthetic absorbent gelling polymers are disclosed in U.S. Pat. No. 4,076,663 issued Feb. 28, 1978 to Masuda et al. and U.S. Pat. No. 4,286,082 issued Aug. 25, 1981 to Tsubakimoto et al., both of which are hereby incorporated herein by reference.

Synthetic absorbent gelling materials typically are xerogels which form hydrogels when wetted. The term "hydrogel", however, has commonly been used to also refer to both the wetted and unwetted forms of the material.

As mentioned previously, the high-absorbency material used in the absorbent is generally in the form of discrete particles. The particles can be of any desired shape, for example, spiral or semi-spiral, cubic, rod-like, polyhedral, etc. Shapes having a large greatest dimension/smallest dimension ration, like needles: flakes and fibers, are also contemplated for use herein. Conglomerates of particles of absorbent gelling material may also be used in the absorbent.

Desired for use are particles having an average size of from about 20 microns to about 1 millimeter. "Particle size" as used herein means the hydrophilic fibers and high-absorbency particles can be configured to form an average composite basis weight which is within the range of about 50-1500 gsm. In certain aspects of the invention, the average composite basis weight is within the range of about 200-1200 gsm, and alternatively is within the range of about 200-1200 gsm, and alternatively is within the range of about 500-800 gsm to provide desired performance. Furthermore, the proportion of high absorbency particles can range from about 0 to about 100% and the proportion of fibrous material from about 0 to about 100%. Additionally, high absorbency fibers can be used such as Oasis Type 121 and Type 122 superabsorbent fibers available from Technical Absorbent Ltd., Grimsby, Lincolnshire, United Kingdom.

The retention portion 70 has laterally opposed side edges 74 and preferably can be made of a single or dual layer of absorbent material. The retention portion preferably has an hour-glass shape with enlarged end regions. Alternatively, the retention portion can include a folded or multi-layered configuration. The retention portion preferably has a length substantially equal to, or slightly shorter than, the length of the absorbent composite. The retention portion can include one or more barrier layers attached to the absorbent material. In one embodiment, an upper tissue substrate 88 is disposed adjacent the retention portion. Alternatively, a lower tissue substrate can be disposed adjacent an opposite side of the retention portion, or the tissue can completely envelope the retention position.

Referring to FIG. 1, the opposite garment side of the end regions 56, 58 of the absorbent composite, and in particular, the outer, garment side surface of the backsheet 68, are secured to the bodyside surface of the longitudinally opposed crotch ends of the first and second body panels 4, 6. It should be understood that the absorbent composite can be secured using any of the methods of attachment described above, including for example various adhesives 77, stitching or other bonding methods. The absorbent composite can be secured to the body panels with any configuration of attachment lines, swirls, patterns, spots, etc., or can be a full and continuous attachment therebetween.

Although the present invention has been described with reference to preferred embodiments, those skilled in the art will recognize that changes may be made in form and detail without departing from the spirit and scope of the invention. As such, it is intended that the foregoing detailed description be regarded as illustrative rather than limiting and that it is the appended claims, including all equivalents thereof, which are intended to define the scope of the invention.

APPENDIX 1

```
Cambridge Instruments QUANTIMET 970 QUIPS/MX: V08.00USER:
ROUTINE : CONWID
    NAME=      CONWID
    DOES=      % AREA. CONVOLUTED WIDTH. &
ANISOTROPY HISTOGRAMS
    AUTH=      B. KRESSNER
    DATE=      17 FEB 85
    DATE=      18 MAY 2000. RECENT ADAPTATION OF
               MBPAS3
    COND=      Cambridge MACROVIEWER: 50 mm EL-
               NIKOR Lens:
```

APPENDIX 1-continued

```
NO extension tubes:   4 100-watt floods; f/8; scanner pole posn
                      43 cm; Plate (¼ in.) glass over 4x5 Polaroid
                      Photos
Enter specimen identity
Scanner              (No. 2 Chalnicon LV = 0.00 SENS=
                      2.33 PAUSE)
Load Shading Corrector ( pattern -MBLOWN)
Calibrate User Specified (Cal Value = 2.962 microns     per pixel)
SUBRTN STANDARD
TOTANISOT    :=       0.
TOTFIELDS    :=       0.
PERCAREA     :=       0.
TOTPERCAR    :=       0.
STAGEX                :=      10000.
STAGEY                :=      10000.
For MONTAGE           =       1 to 2
Stage Move (STAGEX, STAGEY)
Stage Scan            (     X        Y)
    scan origin          STAGEX      STAGEY
    field size           85500.0     56667.0
    no of fields         3           4       )
Scanner         (No. 2 Chalnicon LV=0.00 SENS = 2.33 PAUSE)
For FIELD
Scanner         (No. 2 Chalnicon AUTO-SENSITIVITY LV= 0.00)
Image Frame is Rectangle ( X: 48, Y: 36, W: 800, H: 622, )
Live Frame is Standard Live Frame
Detect 2D       (Darker than 32. Delin)
Amend(OPEN by 1)
Psuedo-Colour Setup - Load Binary A of LUT GREY
    with colour (R 0,G 0,B 0)
Measure field - Parameters into array FIELD
ANISOT        := FIELD ANISOTROPY
ANISOT        := 1./ ANISOT
Distribute COUNT vs ANISOT (Units UNITS )
    into ANISOT from 0.00 to 1.50 into 15 bins, differential
TOTANISOT    :=       TOTANISOT + ANISOT
TOTFIELDS    :=       TOTFIELDS + 1.
PERCAREA     :=       100. * FIELD AREAFRACT
TOTPERCAR    :=       TOTPECAR + PERCAREA
Distribute COUNT vs PERCAREA (Units % AREA )
    into GRAPH1 from 0.00 to 90.00 into 15 bins, differential
Live Frame is Standard Live Frame
Measure feature            AREA PERIMETER LENGTH
                           ROUNDNESS
    into array FEATURE1 ( of 750 features and 7 parameters)
FEATURE1 CALC := ((4. *AREA/PI)^0.50000)
FEATURE1 CALC.C       := 0.9000 * ( ( 4. * AREA /
                          PERIMETER
) * (1. / ROUNDNESS)^ 0.25000 )
FEATURE1 CALC.C := CALC.C /     CAL.CONST
Accept FEATURE1 CALC.C from   3. to      1000.
FEATURE1 CALC.C := CALC.C * CAL.CONST
Distribution of COUNT (Units COUNT     ) v CALC.C (Units
MICRONS )
    from FEATURE1 in HISTO1 from 1.000 to 1000.
    in 15 bins (LOG)
Distribution of AREA (Units SQ MICRONS) v CALC.C (Units
MICRONS )
    from FEATURE1 in HIST04 from 1.000 to 1000.
    in 15 bins (LOG)
FEATURE1 CALC         :=       / CAL.CONST
Accept FEATURE1 CALC from     3. to 1000.
FEATURES1 CALC        :=      CALC * CAL.CONST
Distribution of COUNT (Units COUNT    ) v CALC (Units
MICRONS)
    from FEATURE1 in HIST03 from 1.000 to 1000.
    in 15 bins (LOG)
Stage Step
Next FIELD
Pause Message
PLEASE POSITION THE SECOND SET OF PHOTOS
Pause
Next
Print " "
Print Distribution ( GRAPH1, differential, bar chart, scale = 0.00)
Print "FIELD COUNT vs PERCENT AREA HISTOGRAM"
Print " "
Print "AVE % AREA = ", TOTPERCAR / TOTFIELDS
Print " "
Print " "
```

APPENDIX 1-continued

```
    Print Distribution ( HIST01, differential, bar chart, scale = 0.00 )
    Print "PORE COUNT VS CON WIDTH (um)"
    For LOOPCOUNT = 1 to 15
    Print " "
    Next
    Pause
    Print Distribution ( HIST04, differential, bar chart, scale = 0.00 )
    Print "CUM PORE A% VS CON WIDTH (um)"
    Print " "
    Print " "
    Print Distribution ( ANISOT, differential, bar chart, scale = 0.00 )
    Print "# OF FIELDS vs ANISOTROPY"
    Print " "
    Print " "
    Print "AVERAGE PORE ANISOTROPY (TAN THETA) = " ,
TOTANISOT / TOTFIELDS
    Print " "
    Print "TOTAL SCANNED AREA = " , CL, FRAREA *
FIELDNUM / (1. * 10.^8.). " SQ CM"
    For LOOPCOUNT = 1 to 8
    Print " "
    Next
    END OF PROGRAM
```

APPENDIX 2

```
Cambridge Instruments QUANTIMET 970 QUIPS/MX: V08.02 USER:
ROUTINE: FUZZIO
NAME =         FUZZB
DOES =         PR/EL ON TISSUES; GETS HISTOGRAM
AUTH =         B. E. KRESSNER
DATE =         10 DEC 97
COND =         MACROVIEWER; DCI 12X12; FOLLIES PINK
    FILTER; 3X3 MASK 60 MM MICRO-NIKKO,F/4; 20
    MM EXTENSION TUBES; 2 PLATE (GLASS)
    FIXTURE MICRO-NIKKOR AT FULL EXTENSION
    FOR MAX MAG!!!!
    ROTATE CAM 90 deg SO THAT IMAGE ON RIGHT
    SIDE!!
    ALLOWS TYPICAL PHOTO
Enter specimen identity
Scanner       (No. 1 Chalnicon LV= 0.00 SENS= 2.36 PAUSE)
Load Shading Corrector( pattern - FUZZ7 )
Calibrate User Specified (Cal Value - 9.709 microns     per pixel)
SUBRTIN STANDARD
TOTPREL      :=      0.
TOTFIELDS    :=      0.
PHOTO        :=      0.
MEAN:=        0.
If PHOTO = 1. then
Pause Message
WANT TYPICAL PHOTO (1 YES; 0 NO)*
Input PHOTO
Endif
If PHOTO = 1. then
Pause Message
INPUT MEAN VALUE FOR PR/EL
Input MEAN
Endif
For SAMPLE =          1 to 2
If SAMPLE = 1. then
STAGEX       := 36000.
STAGEY       := 144000.
Stage Move (STAGEX,STAGEY)
Pause Message
please position fixture
Pause
STAGEX       := 120000.
STAGEY       := 144000.
Stage Move (STAGEX,STAGEY)
Pause Message
please focus
Detect 2D      (Darker than 54, Delin PAUSE)
STAGEX       := 36000.
STAGEY       := 144000.
Endif
If SAMPLE = 2. then
```

APPENDIX 2-continued

```
STAGEX       := 120000.
STAGEY       := 44000.
Stage Move (STAGEX,STAGEY)
Pause Message
please focus
Detect 2D     ( Darker than 54, Delin)
STAGEX       := 36000.
STAGEY       := 44000.
Endif
StageMove ( STAGEX,STAGEY)
Stage Scan (       X        Y
           scan origin    STAGEX        STAGEY
           field size     6410.0        78000.0
           no of fields   30            1 )
For FIELD
If TOTFIELDS + 30. then
Scanner (No. 1 Chalnicon AUTO-SENSITIVITY LV=0.01)
Endif
Live Frame is Standard Image Frame
Image Frame is Rectangle( X: 26, Y: 37, W: 823, H: 627, )
Scanner         (No. 1 Chalnicon AUTO-SENSITIVITY LV=0.01 )
Image Frame is Rectangle ( X: 48, Y: 37, W: 803, H: 627,)
Detect 2D       (Darker than 54, Delin )
Amend( OPEN by 0 )
Measure field - Parameters into array FIELD
BEFORPERI := FIELD PERIMETER
Amend( OPEN by 10)
Measure field - Parameters into array FIELD
AFTPERIM:= FIELD PERIMETER
PROVEREL:= ((BEFORPERI - AFTPERIM) / (I.FRAME.H *
CAL.CONST))
TOTPREL    := TOTPREL + PROVEREL
TOTFIELDS:= TOTFIELDS + 1.
If PHOTO~1. then
If PROVEREL > (0.95000 * MEAN ) then
If PROVEREL < (1.0500 * MEAN ) then
Scanner (No. 1 Chalnicon AUTO-SENSITIVITY LV = 0.01 PAUSE)
Detect 2D ( Darker than 53 and Lighter than 10, Delin PAUSE)
Endif
Endif
Endif
Distribute COUNT vs PROVEREL (Units MM/MM     )
           into GRAPH from 0.00 to 5.00 into 20 bins, differential
Stage Step
Next FIELD
Next
Print " "
Print "AVE PR-OVER-EL (UM/UM)=" , TOTPREL / TOTFIELDS
Print " "
Print "TOTAL NUMBER OF FIELDS =" , TOTFIELDS
Print " "
Print "FIELD HEIGHT (MM)=",I.FRAME.H * CAL.CONST / 1000
Print " "
Print " "
Print Distribution ( GRAPH, differential, bar chart, scale= 0.00)
For LOOPCOUNT = 1 to 26
Print " "
Next
END OF PROGRAM
```

What is claimed is:

1. An absorbent garment comprising:

a body panel comprising a layer of non-woven spunbond material having a pattern of discrete bonded areas, wherein said body panel has a non-elasticized and non-gathered area; and a hook-type fastener member comprising a high density array of hooks with a hook density of at least 60 hooks per square centimeter, wherein at least a portion of said array of hooks is directly engaged with said discrete bonded areas of said non-woven spunbond material at said non-elasticized and non-gathered area of said body panel;

wherein said layer of non-woven spunbond material comprises a first layer of non-woven spunbond material, and further comprising a second layer of non-woven spunbond material, wherein said first and second layers of non-woven spunbond material are connected directly to each other free of any intervening layers at said non-elasticized and non-gathered area.

2. The absorbent garment of claim 1 wherein said first and second layers of non-woven spunbond material are connected directly to each other with said pattern of discrete bonded areas.

3. The absorbent garment of claim 1 wherein said layer of non-woven spunbond material comprises a prebonded spunbond material, and wherein said pattern of discrete bonded areas comprises secondary bonded areas.

4. The absorbent garment of claim 1 wherein said hook members each include a stem and a head at an end of said stem.

5. The absorbent garment of claim 4 wherein said head is a circular disc.

6. The absorbent garment of claim 4 wherein said hook-type fastener member has a base supporting an opposite end of said stem, and wherein said head has an outer surface at least a portion of which is formed at an angle to a surface of said base.

7. The absorbent garment of claim 1 wherein said body panel is a front body panel and further comprising a rear body panel, wherein opposite side edges of said front and rear body panels are joined to form a side seam.

8. The absorbent garment of claim 7 wherein said hook-type fastener member comprises a carrier member secured to said front body panel in front of said side seam.

9. The absorbent garment of claim 8 wherein said front body panel comprises a pair of side portions defining said opposite side edges mounted to said opposite side edges of said rear body panel, and a landing member extending between said side portions.

10. The absorbent garment of claim 9 wherein said landing member and said side portions are not connected.

11. The absorbent garment of claim 9 wherein said landing member and said side portions are separated by a line of weakness.

12. The absorbent garment of claim 7 further comprising an absorbent composite extending between and secured to said front and rear body panels.

13. The absorbent garment of claim 1 wherein said body panel comprises a plurality of elastic members forming an elasticized area.

14. The absorbent garment of claim 13 wherein said elasticized area is formed along an upper, waist portion of said body panel.

15. The absorbent garment of claim 13 wherein said elasticized area is formed along a lower, leg portion of said body panel.

16. The absorbent garment of claim 1 wherein between about 5% and 25% of said non-woven spunbond material comprises said bonded area.

17. The absorbent garment of claim 1 wherein said layer of said non-woven spunbond material is made of 100% polypropylene and has a basis weight of between about 0.3 osy and about 1.0 osy.

18. The absorbent garment of claim 1 wherein said layer of said non-woven spunbond material forms and defines an entirety of an outer, garment-side surface of said body panel.

19. The absorbent garment of claim 18 wherein said hook-type fastener member is secured to said outer, garment-side surface of said body panel.

20. The absorbent garment of claim 1 wherein said non-woven spunbond material has a roughness average less than 100 um.

21. The absorbent garment of claim 1 wherein said non-woven spunbond material has an average fuzz-on-edge of less than 0.50.

22. The absorbent garment of claim 1 wherein said non-woven spunbond material is a bonded-carded material.

* * * * *